United States Patent
Duvall et al.

(10) Patent No.: US 12,201,644 B2
(45) Date of Patent: *Jan. 21, 2025

(54) CONJUGATION OF LIPOPHILIC ALBUMIN-BINDING MOIETY TO RNA FOR IMPROVED CARRIER-FREE IN VIVO PHARMACOKINETICS AND GENE SILENCING

(71) Applicant: Vanderbilt University, Nashville, TN (US)

(72) Inventors: Craig L. Duvall, Nashville, TN (US); Samantha M. Sarett, Nashville, TN (US); Thomas A. Werfel, Nashville, TN (US)

(73) Assignee: Vanderbilt University, Nashville, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 17/474,765

(22) Filed: Sep. 14, 2021

(65) Prior Publication Data

US 2022/0241317 A1    Aug. 4, 2022

Related U.S. Application Data

(63) Continuation of application No. 15/671,131, filed on Aug. 7, 2017, now Pat. No. 11,147,827.

(60) Provisional application No. 62/371,619, filed on Aug. 5, 2016.

(51) Int. Cl.
| | |
|---|---|
| *C07H 21/04* | (2006.01) |
| *A61K 9/00* | (2006.01) |
| *A61K 31/7105* | (2006.01) |
| *A61K 47/54* | (2017.01) |
| *C07K 14/76* | (2006.01) |
| *C12N 15/11* | (2006.01) |

(52) U.S. Cl.
CPC ........ *A61K 31/7105* (2013.01); *A61K 9/0019* (2013.01); *A61K 47/543* (2017.08); *C07K 14/76* (2013.01); *C12N 15/111* (2013.01); *C12N 2310/14* (2013.01); *C12N 2310/141* (2013.01); *C12N 2310/3515* (2013.01); *C12N 2320/32* (2013.01)

(58) Field of Classification Search
None
See application file for complete search history.

(56) References Cited

U.S. PATENT DOCUMENTS

| | | | | |
|---|---|---|---|---|
| 11,104,899 B2* | 8/2021 | Prakash | ............... | C12N 15/113 |
| 2008/0311040 A1* | 12/2008 | Berry | ..................... | A61P 43/00 |
| | | | | 435/375 |
| 2015/0231302 A1 | 8/2015 | Duvall et al. | | |
| 2015/0283254 A1 | 10/2015 | Duvall et al. | | |
| 2016/0058876 A1 | 3/2016 | Duvall et al. | | |
| 2016/0175265 A1 | 6/2016 | Duvall et al. | | |

OTHER PUBLICATIONS

Siu, King S., et al. ("Single-walled carbon nanotubes noncovalently functionalized with lipid modified polyethylenimine for siRNA delivery in vitro and in vivo." Bioconjugate chemistry 25.10 (2014): 1744-1751).*

Kim, Hyun-Ki, et al.(Enhanced siRNA delivery using cationic liposomes with new polyarginine-conjugated PEG-lipid. International journal of pharmaceutics 392.1-2 (2010): 141-147).*

Van Delft, Pieter, et al. ("Synthesis of oligoribonucleic acid conjugates using a cyclooctyne phosphoramidite." Organic letters 12.23 (2010): 5486-5489.*

Hiki et al. ("A facile synthesis of azido-terminated heterobifunctional poly (ethylene glycol) or "click" conjugation." Bioconjugate chemistry 18.6 (2007): 2191-2196).*

Kanasty et al. ("Sequence-defined oligomers from hydroxyproline building blocks for parallel synthesis applications." Angewandte Chemie International Edition 55.33 (2016): 9529-9533).*

Bienk K, et al., An albumin-mediated cholesterol design-based strategy for tuning sirna pharmacokinetics and gene silencing. J Control Release (2016) 232:143-151.

Kamphorst JJ, et al., Human pancreatic cancer tumors are nutrient poor and tumor cells actively scavenge extracellular protein. Cancer Res (2015) 75:544-553.

Lau S, et al., Enhanced extravasation, stability and in vivo cardiac gene silencing via in situ siRNA-albumin conjugation., Mol Pharm (2012) 9:71-80.

* cited by examiner

*Primary Examiner* — Kimberly Chong
(74) *Attorney, Agent, or Firm* — Stites & Harbison PLLC; Richard S. Myers, Jr.

(57) ABSTRACT

Provided herein are compounds and methods for gene silencing. The compound includes a RNA directly conjugated to an albumin-binding group. The method includes administering a compound comprising a RNA directly conjugated to an albumin-binding group to a subject in need thereof.

3 Claims, 30 Drawing Sheets

CONJUGATION OF LIPOPHILIC ALBUMIN-BINDING MOIETY TO RNA FOR IMPROVED CARRIER-FREE IN VIVO PHARMACOKINETICS AND GENE SILENCING

RELATED APPLICATIONS

This application is a continuation of U.S. patent application Ser. No. 15/671,131, filed Aug. 7, 2017, and now allowed, which claims the benefit of U.S. Provisional Application Ser. No. 62/371,619, filed Aug. 5, 2016, the entire disclosures of which are incorporated herein by this reference.

GOVERNMENT INTEREST

This invention was made with government support under grant number R01EB019409 awarded by the National Institutes of Health (NIH), and grant numbers 1349604, 1445191, 1445197, and 0909667 awarded by the National Science Foundation (NSF). The government has certain rights in the invention.

TECHNICAL FIELD

The presently-disclosed subject matter generally relates to products and methods for RNA treatment and administration. More specifically, the presently-disclosed subject matter relates to conjugated RNA compounds, methods of administering RNA compounds, and methods of treating diseases with RNA compounds.

BACKGROUND

Small interfering RNA (siRNA) has received significant attention in connection with RNAi therapies due to its capacity to silence traditionally undruggable targets. However, in vivo delivery barriers have typically limited clinical translation of siRNA, especially for nonhepatic targets such as solid tumors. More specifically, clinical translation of therapies based on small interfering RNA (siRNA) has been hampered by its comprehensively poor pharmacokinetic properties that necessitate molecule modifications and complex delivery strategies. In particular, systemic delivery of siRNA has been a challenge due to rapid renal clearance from circulation, which leads to removal through the urine and provides only minimal bioavailability in target tissues. This rapid renal clearance limits the use of siRNA as a cancer therapeutic, as long vascular circulation time following intravenous injection is the primary predictor of tumor biodistribution.

To overcome these delivery barriers, prior efforts have typically focused on improving siRNA delivery through encapsulation in nanoparticulate carrier systems. While a broad range of nanocarrier systems have shown the capacity to improve in vivo pharmacokinetics of siRNA, most of these carrier systems have not achieved clinical relevancy. This is due, in part, to their complex nature, preferential uptake by clearance organs which limits delivery to target sites, variable distribution throughout target sites, and/or low therapeutic indices resulting from nonspecific, carrier-associated toxicities.

More recently, siRNA conjugates have emerged as an alternative to nanocarrier-mediated delivery, offering the possibility of improving siRNA pharmacokinetics without requiring a more complex delivery vehicle. For example, Alnylam Pharmaceuticals has demonstrated high gene silencing potency of a trivalent N-Acetylgalactosamine (GalNAc) siRNA conjugate, which binds with high specificity and affinity to the asialoglycoprotein receptor on hepatocytes. Carrier-free gene silencing has also been achieved in the liver with siRNA-cholesterol conjugates. However, siRNA conjugates that efficiently deliver to nonhepatic tissues have yet to be developed.

Accordingly, there remains a need for methods and products that improve the in vivo pharmacokinetics and gene silencing of siRNA, particularly in nonhepatic tissue.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

In some embodiments, the presently-disclosed subject matter is directed to a compound comprising a RNA directly conjugated to an albumin-binding group. In one embodiment, the albumin-binding group is hydrophobic. In another embodiment, the albumin-binding group is hydrophobic and anionic. In one embodiment, the albumin-binding group is a divalent lipidic moiety. In another embodiment, the divalent lipid moiety is a diacyl lipid. In a further embodiment, the divalent lipidic moiety comprises 1,2-distearoyl-sn-glycero-3-phosphoethanolamine-N-[azido(polyethylene glycol)-2000] ($L_2$).

In some embodiments, the RNA is siRNA or miRNA. In one embodiment, the siRNA comprises a functionalized siRNA. In another embodiment, the functionalized siRNA is functionalized with a dibenzocyclooctyne moiety. In some embodiments, the compound is complexed with albumin.

Also provided herein, in some embodiments, is a compound comprising siRNA functionalized with a dibenzocyclooctyne moiety and directly conjugated to 1,2-distearoyl-sn-glycero-3-phosphoethanolamine-N-[azido(polyethylene glycol)-2000].

Further provided herein, in some embodiments, is a method of gene silencing, the method comprising administering a compound comprising a RNA directly conjugated to an albumin-binding group to a subject in need thereof. In one embodiment, the albumin-binding group is hydrophobic. In another embodiment, the albumin-binding group is hydrophobic and anionic. In one embodiment, the albumin-binding group is a diacyl lipid. In one embodiment, wherein the albumin-binding group comprises 1,2-distearoyl-sn-glycero-3-phosphoethanolamine-N-[azido(polyethylene glycol)-2000] ($L_2$). In some embodiments, the RNA is siRNA or miRNA. In some embodiments, the siRNA comprises a functionalized siRNA.

In some embodiments, the administering comprises intravenous administration. In some embodiments, the method further comprises treating cancer in the subject.

DESCRIPTION OF EXEMPLARY EMBODIMENTS

Figure 1A:
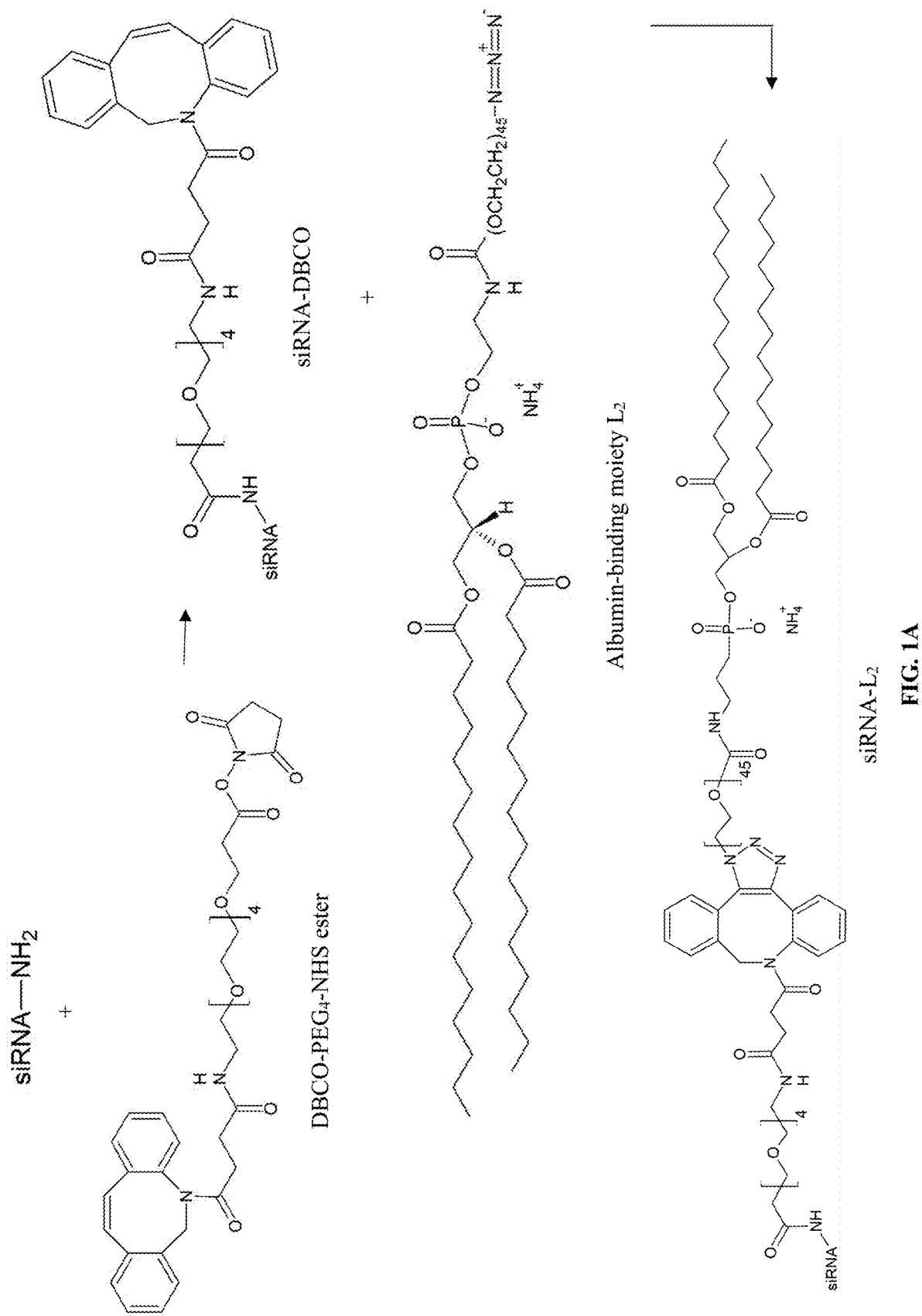
FIGS. 1A-E show graphs and images illustrating that successfully synthesized and purified siRNA-L2 conjugate binds to albumin. (A) Abbreviated structures of reactants and final oligonucleotide-L2 conjugate. Synthesis scheme is twostep; 1) siRNA-NH2+DBCO-PEG4-NHS ester, 2) siRNA-DBCO+DSPE-PEG(2000)-azide. (B) MALDI-TOF mass spectrometry of the original amine-modified siRNA, the DBCO intermediate, and the L2 conjugate. (C) HPLC purification of siRNA-L2 conjugate from reactant precursors. (D) L2 conjugation does not impact siRNA silencing efficacy. A comparison of siRNA and siRNA-L2 silencing from in vivo jetPEI at a dose of 100 nM; n of 5, standard error shown. (E) Albumin binding measured by gel stained for siRNA (Top) and protein (Bottom). siRNA-L2 migrates as a micellar population alone and comigrates with albumin, whereas unmodified siRNA does not migrate with albumin. Note that albumin shows up as multiple bands due to running in nondenaturing, native gel conditions.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "small interfering RNA" or "siRNA" refers to a double-stranded RNA molecule, 20-25 base pairs in length, with phosphorylated 5' ends and hydroxylated 3' ends including two overhanging nucleotides. siRNA interfere with the expression of genes having complementary nucleotide sequences by degrading mRNA after transcription.

As used herein, the term "microRNA" or "miRNA" refers to ribonucleic acid sequences that when made synthetically are structurally the same as siRNA, but are synthesized based on a sequence that is expressed in vivo rather than a sequence that is "discovered" and fully synthetic like siRNA.

The presently-disclosed subject matter includes methods and products for administration of RNA. In one embodiment, the product includes an RNA conjugate. In another embodiment, the RNA conjugate includes a RNA molecule directly conjugated to an albumin-binding group.

The RNA molecules include any suitable double-stranded RNA molecules, such as, but not limited to, small interfering RNA (siRNA) and/or microRNA (miRNA). For example, in one embodiment, the albumin-binding group may be conjugated to the 3' end of the passenger strand of any siRNA and/or miRNA molecule. Although described generally with respect to conjugation of the 3' end of the passenger (sense) strand, as will be appreciated by those skilled in the art, the disclosure is not so limited and includes conjugation to other termini such as the 5' end of the passenger strand, the 3' end of the guide/antisense strand, or the 5' end of the guide/antisense strand.

The albumin-binding groups include, but are not limited to, any suitable hydrophobic and/or anionic compound. Suitable albumin-binding groups may include hydrophobic molecules and/or lipids, such as palmitate; monacyl chains of varied lengths; diacyl chains of varied lengths; chains having varied levels of saturated (double) bonds; diacids; aromatic ligands; heterocyclic ligands, such as evans blue; anionic molecules; molecules that are both anionic and hydrophobic, including anionic and hydrophobic peptides; aptamers; or a combination thereof. For example, in one embodiment, the RNA is directly conjugated to a divalent lipidic moiety. In another embodiment, the RNA is directly conjugated to a C18 diacyl lipid. In a further embodiments, where the albumin-binding group includes a diacid, the hydrophobic chain thereof has a carboxylic acid end functionality that improves albumin binding.

In one embodiment, the RNA molecule is conjugated to the albumin-binding group through one or more crosslinkers. In another embodiment, using one or more of the crosslinkers disclosed herein facilitates conjugation of any suitable RNA molecule to any suitable albumin-binding group. The crosslinker(s) include any suitable linker capable of coupling the RNA to the albumin-binding group. Suitable crosslinkers include, but are not limited to, heterobifunctional linkers, polyethylene glycol (PEG) linkers having a molecular weight of between 0 and 40,000, peptide linkers, or a combination thereof. For example, suitable PEG crosslinker include PEG molecules having 45 repeat units (i.e., a molecular weight of about 2000 g/mol), 24 repeat units, 12 repeat units, 6 repeats, any other suitable number of repeat units providing a molecular weight within the range disclosed herein, or any combination, sub-combination, range, or sub-range thereof. Other suitable non-PEG crosslinkers include, for example, cleavable peptide linkers, such as cathepsin, which promote release of siRNA for albumin binder in the endosome; peptides with endosome disruptive function, such as melittin; peptides that serve as a simple spacer, such as polyglycine; peptides that cooperate with the albumin-binding group to improve albumin binding, such as negatively charged and hydrophobic amino acid containing sequences; cell penetrating peptides that promote cell uptake of the cargo, such as the CPP "Tat" or poly(arginine); or a combination thereof.

In some embodiments, the RNA is functionalized and/or modified prior to conjugation. In one embodiment, modifying and/or functionalizing the RNA includes attaching a linker thereto. In another embodiment, the linker is attached through any suitable method, including, but not limited to, "click" (octyne-azide) chemistry, N-hydroxysuccinimide (NHS)-amine reaction, thiol-maleimide reaction, guest-host interaction (e.g., biotin-streptavidin or cyclodextrin-adamantane), or a combination thereof. In a further embodiment, attaching the linker includes first modifying the RNA with an amine, then reacting the amine modified RNA with the linker. For example, attaching a N-hydroxysuccinimide (NHS) ester/octyne linker to an siRNA may include modifying the siRNA with an amine, and subsequently reacting the amine-modified siRNA with a dibenzocyclooctyne-PEG4-N-hydroxysuccinimidyl ester.

Additionally or alternatively, the albumin-binding group may be modified and/or selected to bind the RNA and/or functionalized RNA to form the RNA conjugate. For example, in one embodiment, albumin-binding group includes or is modified to include an azide functional diacyl molecule that is arranged and disposed to react with an octyne on the functionalized RNA. In a more specific example, the functionalized RNA is directly conjugated to 1,2-distearoyl-sn-glycero-3-phosphoethanolamine-N-[azido (polyethylene glycol)-2000] (DSPE-PEG$_{2000}$-azide, or L$_2$) to form the RNA conjugate, termed siRNA-L$_2$. Although described above with regard to an azide functional diacyl reacting with an octyne, as will be appreciated by those skilled in the art, the disclosure is not so limited and may include other methods of conjugation including the use of other reactive groups on the albumin binder, such as direct use of an amine or carboxylic acid for attachment.

In some embodiments, the siRNA conjugate, such as siRNA-L$_2$, binds the serum protein albumin via interaction with a two-tailed lipid chain. In one embodiment, the binding of the siRNA conjugate to the serum protein albumin enhances the pharmacokinetic properties of the siRNA as compared to an unmodified siRNA and/or existing nanocarrier. In another embodiment, enhancing the pharmacokinetic properties includes increasing the circulation half-life and/or bioavailability of the siRNA, as compared to existing nanocarriers and/or unmodified siRNA. Additionally or alternatively, enhancing the pharmacokinetic properties may include increasing the quantity of cellular or tumor accumulation, increasing the homogeneity of cellular or tumor accumulation, increasing resistance to nucleases, and/or permitting increased dosing amount with decreased toxicity as compared to unmodified siRNA and/or existing nanocarriers.

For example, in one embodiment, in contrast to existing nanocarries which provide a tumor:liver accumulation ratio of less than 3:1, the conjugation of L$_2$ provides a tumor:liver accumulation ratio of at least 5:1, at least 10:1, at least 20:1, at least 30:1, at least 40:1, or any combination, sub-combination, range, or sub-range thereof. In another embodiment, the siRNA-L$_2$ conjugate provides uptake in at least at least 60%, at least 65%, at least 70%, at least 75%, at least 80%, at least 85%, at least 90%, at least 95%, at least 96%, at least 97%, at least 98%, and/or at least 99% of tumor cells.

In certain embodiments, the conjugation of L$_2$ provides at least a 4-fold increase in circulation half-life, at least a 6-fold increase in bioavailability, and/or decreased renal accumulation as compared to unmodified siRNA and/or existing nanoparticle carriers. For example, in one embodiment, the conjugation of L$_2$ increases circulation half-life at least 7.5-fold and/or bioavailability at least 13-fold as compared to unmodified siRNA. In another embodiment, the conjugation of L$_2$ increases tumor accumulation at least 19-fold and/or per-tumor-cell uptake at least 46-fold as compared to existing siRNA nanocarriers.

In addition to enhancing the pharmacokinetic properties as discussed above, the conjugation of siRNA to a divalent lipidic moiety maintains or substantially maintains the gene silencing activity of the conjugated siRNA. Accordingly, in some embodiments, the siRNA conjugate provides increased gene silencing as compared to unmodified siRNA and/or existing nanocarriers. Without wishing to be bound by theory, it is believed that the increased circulation time, tumor penetration, and tumor distribution of the siRNA conjugates, along with the maintained or substantially maintained gene silencing activity, facilitate use of the conjugate as a cancer therapeutic.

Also provided herein, in some embodiments, is a method of gene silencing. In one embodiment, the method includes administering one or more of the siRNA conjugates disclosed herein to a subject in need thereof. The siRNA conjugates may be administered by any suitable process, including, but not limited to, intravenous (i.v.) administration. In another embodiment, after administration, the siRNA conjugates bind to endogenous albumin, which provides the enhanced pharmacokinetics discussed herein. Additionally or alternatively, at least one of the siRNA conjugates may be pre-complexed with albumin prior to administration. In a further embodiment, the siRNA conjugates are administered without a nanocarrier or other encapsulation/carrier compound.

In certain embodiments, because albumin is not trafficked to the liver, the siRNA conjugate mediates gene silencing at alternative targets where accumulation occurs as a result of long circulation time. In one embodiment, the alternative target is a tumor. For example, siRNA-L$_2$ mediates enhanced gene silencing in vitro in MDA-MB-231 breast cancer cells compared to unmodified siRNA. Accordingly, in some embodiments, the method of gene silencing further includes treating a disease in a subject in need thereof. The disease includes any disease state that can be treated through effective i.v. RNAi therapy. For example, one therapeutic aim includes the treatment of tumors. In another example, the increased vascular permeability of the tumors leads to increased accumulation of long-circulating entities having a size of less than about 200 nm, less than about 100 nm, less than about 50 nm, less than about 25 nm, less than about 20 nm, less than about 15 nm, less than about 10 nm, less than about 9 nm, less than about 8 nm, less than about 7 nm, about 7 nm, or any combination, sub-combination, range, or sub-range thereof.

In some embodiments, the siRNA conjugate is modified to provide and/or facilitate targeting siRNA-$L_2$ to a particular desired cell type or physiological site and/or to mediate endosomal escape. Additionally or alternatively, the delivery strategy of the siRNA conjugate may be modified to provide and/or facilitate targeting siRNA-$L_2$ to a particular desired cell type or physiological site and/or to mediate endosomal escape.

EXAMPLES

Example 1

Significance

This example describes a diacyl lipid-modified siRNA that leverages albumin as an endogenous carrier, resulting in comprehensively enhanced pharmacokinetic properties that translate to greater quantity and homogeneity of tumor accumulation relative to nanocarriers. The albumin-binding siRNA conjugate strategy described herein is synthetically simple and safe at high doses, and thus is a translatable and potentially transformative option for RNAi oncology therapies.

The enhanced permeability and retention (EPR) effect, based upon the high vascular permeability and diminished lymphatic drainage at tumor sites, suggests a preferential tumor accumulation of particles of nanocarrier size (~100 nm). However, the EPR phenomenon as a tumor targeting strategy has recently come under intense scrutiny due to the discrepancy observed between preclinical and clinical efficacy of nanoparticle-based cancer therapeutics. There is a growing appreciation that among wildly heterogeneous human cancers, the EPR effect may be only relevant in select tumor or patient subsets. In particular, the widespread "leakiness" of tumor vasculature, a characteristic of rapidly developing mouse tumor models, has likely been exaggerated in its relevance to slower-forming human lesions. The field of nanomedicine has responded to these realizations with efforts to enhance understanding of nanoparticle performance in animal models, strategies to normalize tumor vasculature, systematic investigations into ideal nanoparticle characteristics, and a focus on smaller (20-30-nm-sized) nanocarriers. Despite the promise of these approaches, the diversity of human cancers necessitates equivalently diverse delivery approaches and opportunity for improvement remains, particularly in the area of enhancing uniformity of tumor distribution.

As an alternative approach to commonly used nanoparticle carriers, the instant inventors leveraged the long-lived endogenous serum protein albumin as an siRNA carrier. This example describes the synthesis of siRNA conjugated to a diacyl lipid moiety (siRNA-$L_2$), which rapidly binds albumin in situ. In comparison with unmodified siRNA, siRNA-$L_2$ exhibited a 5.7-fold increase in circulation half-life corresponding to an 8.6-fold increase in bioavailability and reduced renal accumulation. Benchmarked against leading commercial siRNA nanocarrier in vivo jetPEI, siRNA-$L_2$ achieved 19-fold greater tumor accumulation and 46-fold increase in per-tumor-cell uptake in a mouse orthotopic model of human triple-negative breast cancer.

Additionally, in contrast to nanoparticles that typically exhibit concentration of dose near leaky vessels but not within more avascular tumor regions, resulting in inhomogeneous efficacy and higher potential for incomplete remission and recurrence, the smaller, long-circulating siRNA conjugates provide an alternative that creates more homogeneous therapeutic distribution within tumors. Indeed, the apparent tissue permeability of the serum protein albumin [hydrodynamic size ~7.2 nm] is consistently more than fourfold greater than that of 100-nm liposomes in a variety of mouse models of breast cancer. With respect to the instant conjugates, siRNA-$L_2$ penetrated tumor tissue rapidly and homogeneously; 30 min after i.v. injection, siRNA-$L_2$ achieved uptake in 99% of tumor cells, compared with 60% for jetPEI. Remarkably, siRNA-$L_2$ achieved a tumor:liver accumulation ratio >40:1 vs. <3:1 for jetPEI. The improved pharmacokinetic properties of siRNA-$L_2$ facilitated significant tumor gene silencing for 7 d after two i.v. doses.

Proof-of-concept was extended to a patient-derived xenograft model, in which jetPEI tumor accumulation was reduced fourfold relative to the same formulation in the orthotopic model. The siRNA-$L_2$ tumor accumulation diminished only twofold, suggesting that the superior tumor distribution of the conjugate over nano-particles will be accentuated in clinical situations. These data reveal the immense promise of in situ albumin targeting for development of translational, carrier-free RNAi-based cancer therapies. In particular, it is anticipated that albumin-associated siRNA will show promise as a cancer therapeutic by extending the circulation time of siRNA, enabling efficient tumor tissue penetration, and leveraging the propensity of tumor cells to internalize albumin.

In situ targeting of albumin following i.v. delivery is a viable strategy because endogenous albumin is the most abundant serum protein (>40 mg/mL) and has a circulation half-life of about 20 d. It is also a natural carrier of and has a high affinity for poorly soluble lipids. Although previous work has established the utility of interaction of high- and low-density lipoproteins with cholesterol-conjugated siRNA, the natural trafficking of these lipoproteins concentrates the therapy in the hepatocytes of the liver. The potential of albumin-bound siRNA has been minimally explored. In the unique strategy discussed herein, the capacity of albumin to bind fatty acids is exploited by modifying siRNA with a lipidic moiety designed for high-affinity albumin binding. Through modification of siRNA with a lipidic albumin-targeting agent rather than alternative albumin-binding molecules like peptide domains and a truncated Evans blue, the hydrophobically modified siRNA exhibited improved resistance to nucleases and enhanced cellular internalization. Thus, the strategic choice of modification with an albumin-binding lipid has the potential to confer additional advantages in siRNA stability and cell membrane interactions for uptake and endosomal escape in addition to circulation persistence, tissue penetration, and biodistribution. To investigate the clinical potential of the siRNA conjugate, its efficacy was examined as a systemic RNAi cancer therapeutic by evaluating delivery and gene silencing in translationally relevant models of human triple-negative breast cancer.

Results

Figure 1B:
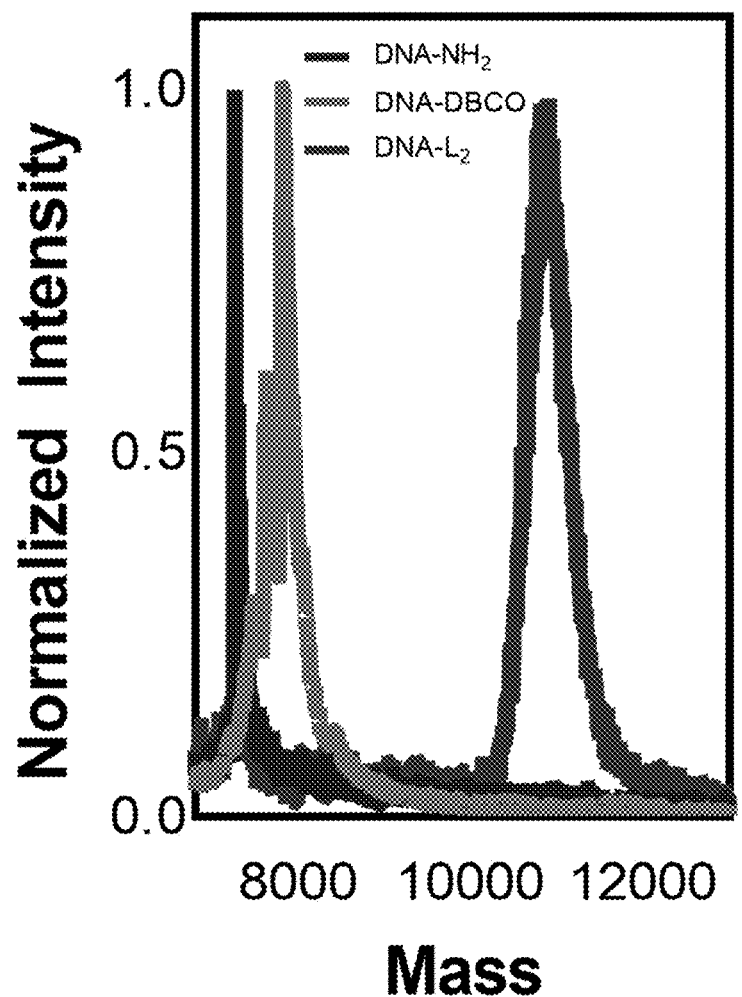
Figure 1C:
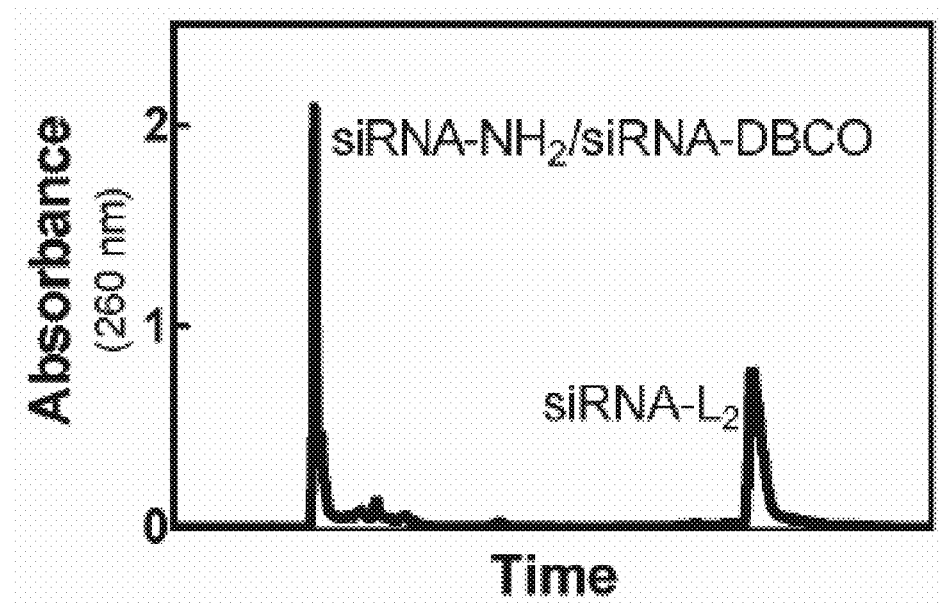
Figure 1D:
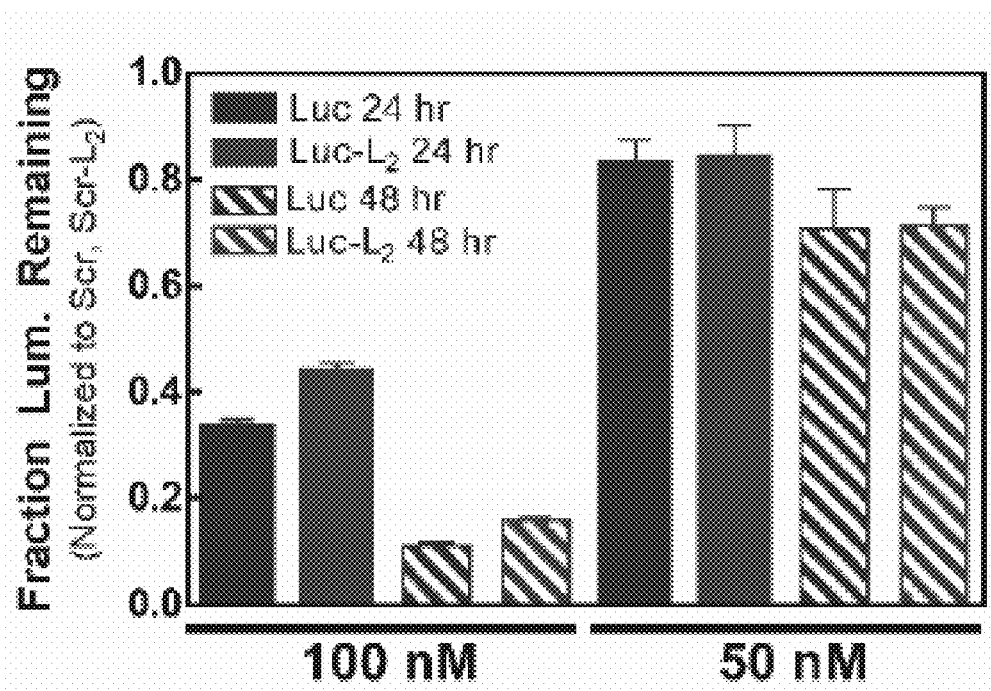

Purified siRNA-L$_2$ Conjugate Binds to Albumin. To synthesize siRNA-L$_2$, a single-stranded amine-modified siRNA was reacted with an NHS ester/octyne heterobifunctional crosslinker and subsequently conjugated with 1,2-distearoyl-sn-glycero-3-phosphoethanolamine-N-[azido(polyethylene glycol)-2000] (DSPE-PEG2000-azide) to generate siRNA-L$_2$ (FIG. 1A). The fully purified L$_2$ conjugates were obtained by reverse-phase chromatography and purity was confirmed by mass spectrometry (FIGS. 1B-C). Following purification, sense strand siRNA-L$_2$ was annealed to the corresponding antisense strand (for imaging studies, the antisense strand was Cy5-labeled). It was confirmed that conjugation of the L$_2$ moiety to siRNA did not significantly impact its inherent gene silencing activity, as demonstrated by in vitro knockdown evaluation of siRNA and siRNA-L$_2$ delivered via the commercial transfection reagent in vivo jetPEI (FIG. 1D).

Figure 1E:
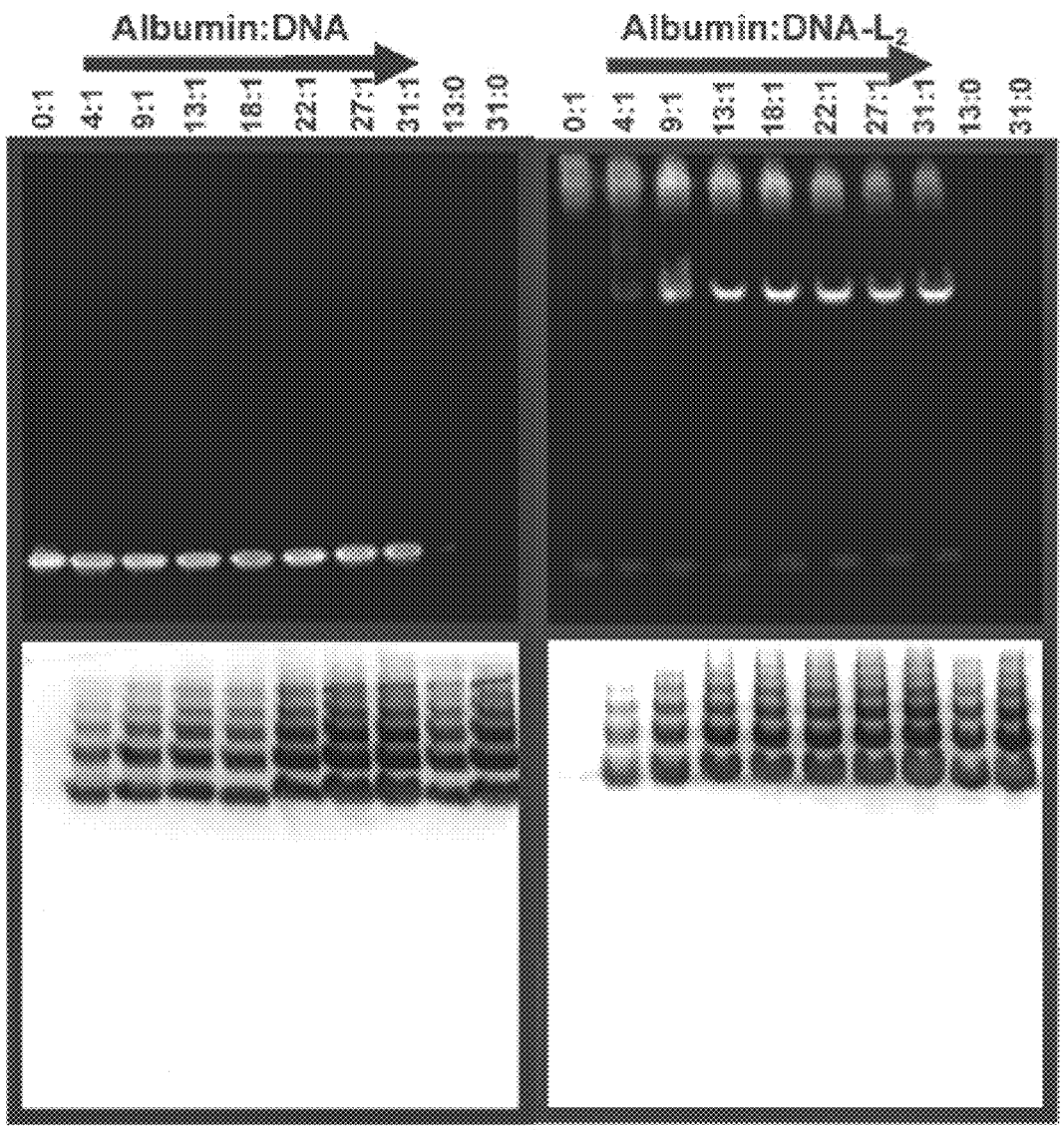
Figure 2A:
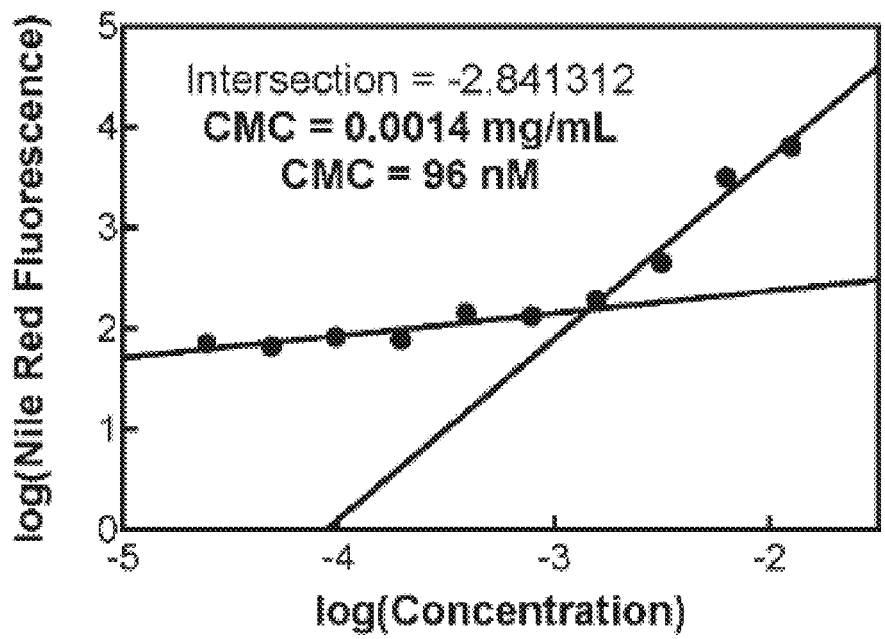
FIG. 2A-B. (A) Critical micelle concentration of siRNA-L2 as determined via Nile Red assay. (B) Isothermal calorimetry (ITC) shows exothermic binding of siRNA-L2 to bovine serum albumin (BSA) with a dissociation constant of 1.38 μM.
Figure 2B:
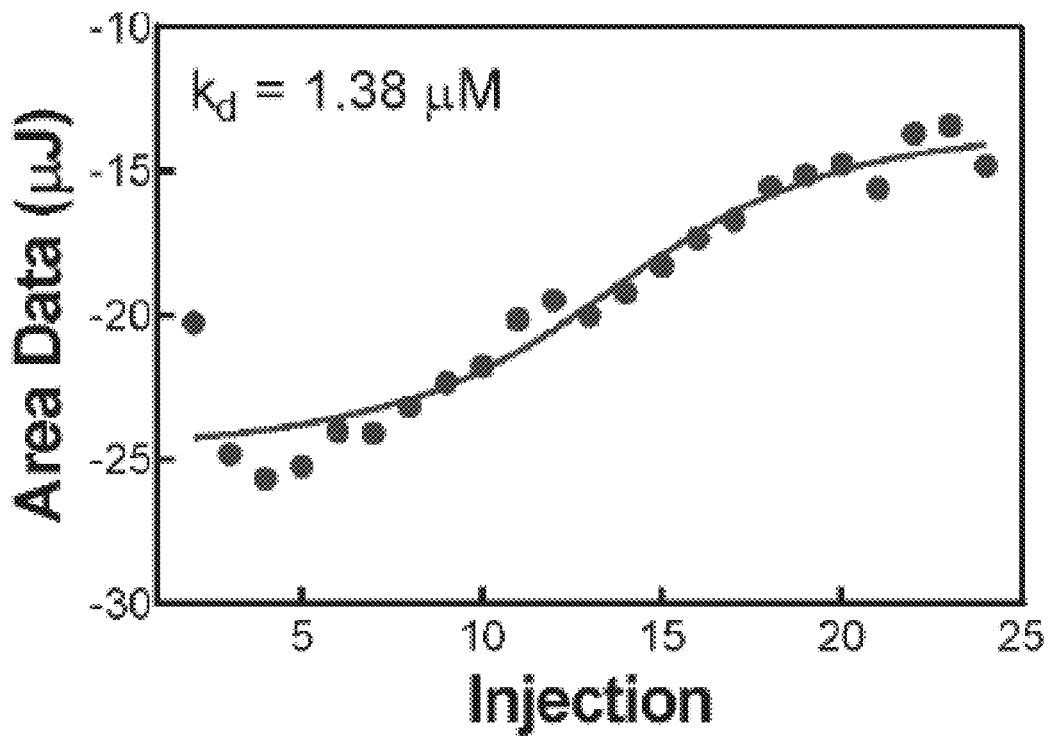
Figure 3A:
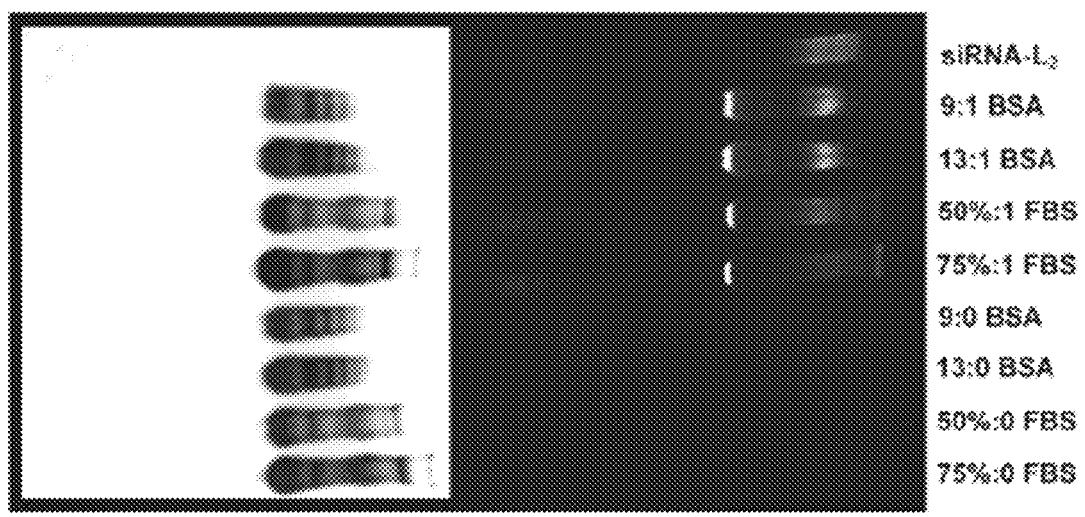
FIGS. 3A-G. Show graphs and images illustrating that conjugation of diacyl lipid to oligonucleotides increases circulation half-life and reduces renal clearance. (A) Evaluation of association of siRNA/siRNA-L2 with BSA or serum albumin in FBS by PAGE gel retardation assay. siRNA-L2 alone (far right) migrates as a micellar population. Bound siRNA-L2 migrates in the same location when mixed with BSA or FBS, suggesting that siRNA-L2 is associating with the albumin component of FBS. Also shown are protein controls of BSA and FBS (left). (B) Cy5-labeled siRNA-L2 and siRNA fluorescence in the blood measured in real time intravitally by confocal microscopy after i.v. injection of CD1 mice. (C) Representative images of fluorescence in mouse blood vessels over time. (D) siRNA-L2 shows association with albumin in vivo. Cy5-labeled siRNA-L2 and siRNA was injected i.v. into CD1 mice and blood was collected after 20 minutes. Serum isolated from blood components was evaluated via PAGE gel retardation assay for the presence of Cy5-labeled oligonucleotide. Mice injected with siRNA had no Cy5 signal in the serum, but mice injected with siRNA-L2 showed faint bands corresponding to the unbound siRNA-L2 and a stronger band corresponding to albumin-bound siRNA-L2. (E) siRNA and siRNA-L2 degrade over time in 60% FBS at 37° C. siRNA-L2 degrades more slowly than siRNA. (F) DNA, DNA-L2 degrade on a similar time scale to siRNA. siRNA-L2. (G) Organ biodistribution of siRNA and siRNA-L2 at 20 min after i.v. injection. n=3, SE shown; ***P<0.001.

The albumin-binding capacity of siRNA-L$_2$ was confirmed using a nondenaturing, native PAGE assay (FIG. 1E). siRNA-L$_2$ alone migrates above the albumin band because it exists as a micellar population at the concentration loaded into the gel (0.05 mg/mL), whereas critical micelle concentration is 1.4 μg/mL (FIG. 2A). As the albumin:siRNA-L$_2$ ratio increases, more siRNA-L$_2$ binds to and migrates with albumin. Unmodified siRNA does not bind to albumin to any degree at any of the concentrations tested. Evaluation of siRNA-L$_2$ binding to albumin via isothermal calorimetry further confirmed spontaneous association of the molecules (dissociation constant was 1.38 μM; FIG. 2B). Binding of L$_2$ conjugates to albumin in the presence of complete serum was also evaluated by gel migration assay, revealing preferential binding to the albumin component of serum (FIG. 3A).

Figure 3B:
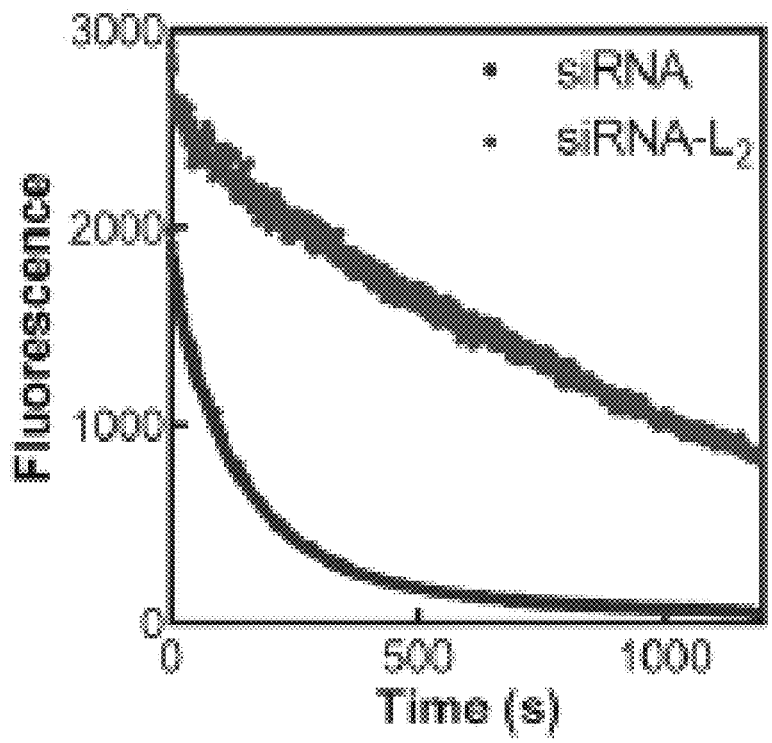
Figure 3C:
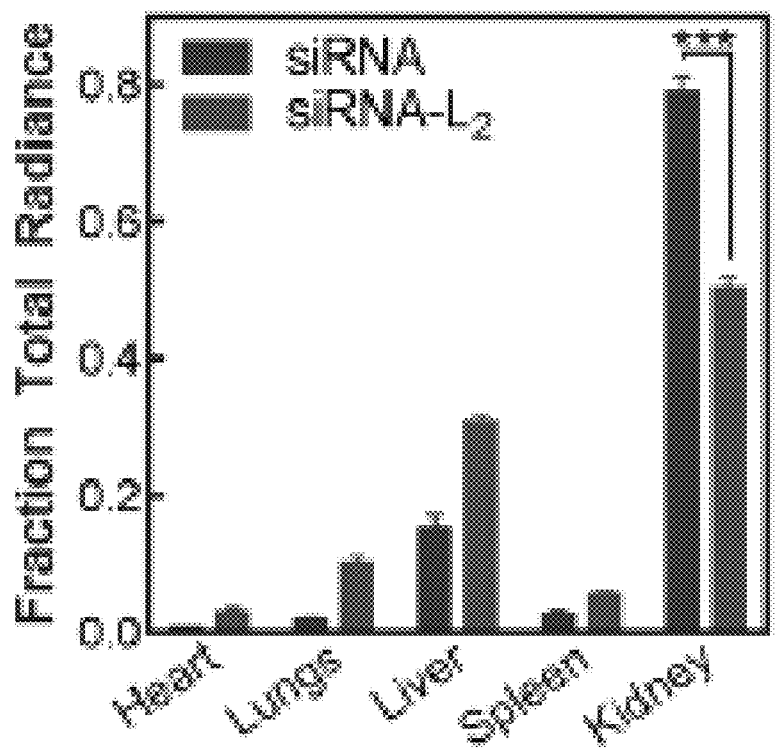
Figure 3D:
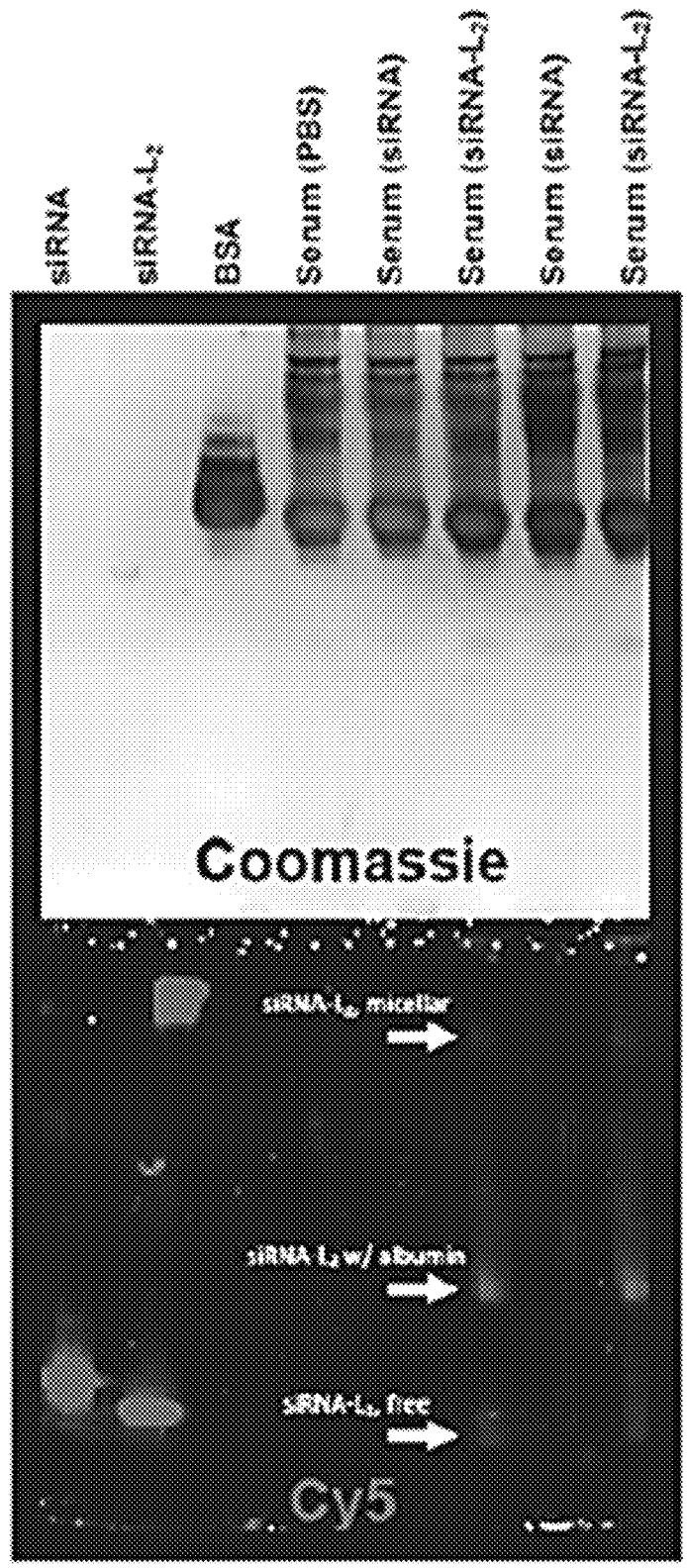
Figure 3E:
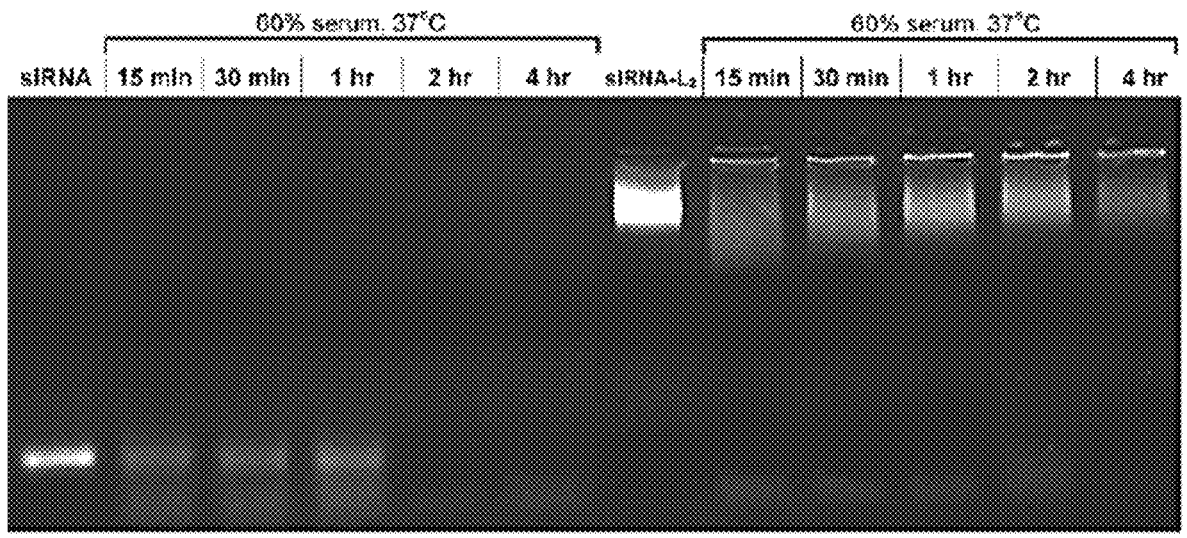
Figure 3F:
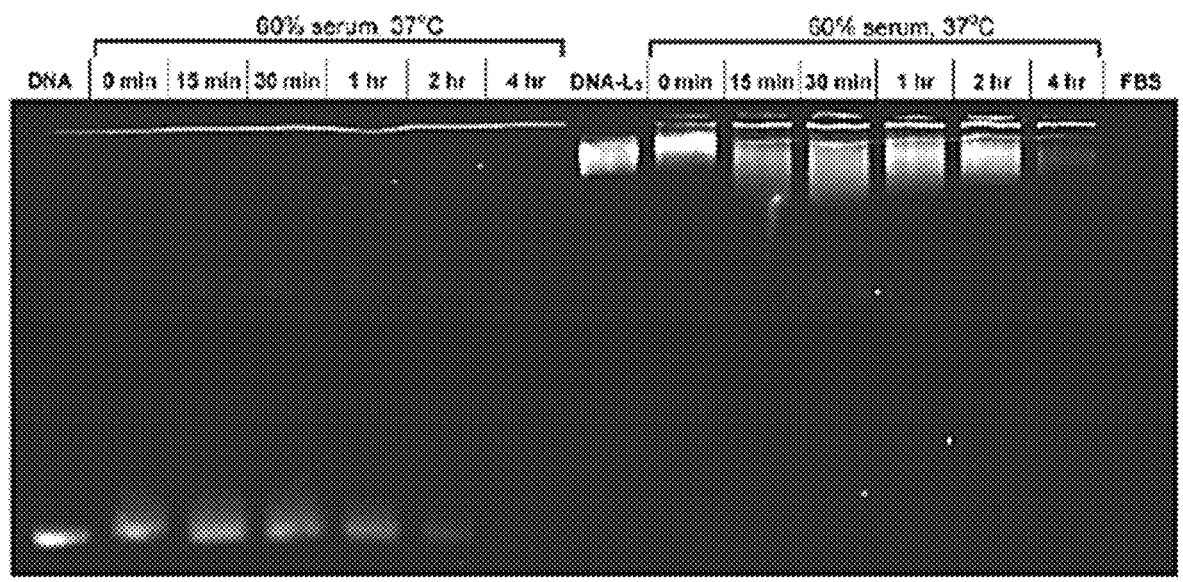

Albumin Binding of siRNA-L$_2$ Enhances Circulation Time and Reduces Rapid Renal Clearance. To characterize the in vivo pharmacokinetics of siRNA-L$_2$ in comparison with unmodified siRNA, circulation persistence was evaluated in real time using intravital confocal microscopy following i.v. injection (Materials and Methods). The circulation half-life$_{(t1/2)}$ of siRNA-L$_2$ was 5.7-fold longer than unmodified siRNA (FIGS. 3B-C and Table 1). Additionally, the area under the curve, a measure of bioavailability of systemically delivered therapeutics, was 8.6-fold greater for the L$_2$-conjugate compared with unmodified oligonucleotide. To evaluate in situ albumin binding, serum samples from mice injected with siRNA-L$_2$ (blood collection at 20 min postinjection) were evaluated via PAGE gel migration assay and revealed the presence of albumin-bound siRNA-L$_2$ (FIG. 3D). These data confirm that albumin acts as a chaperone for siRNA-L$_2$ in vivo and establish that siRNA-L$_2$ association with albumin confers significant improvements in siRNA pharmacokinetics. To support these studies, the time scale of degradation of unmodified and L$_2$-modified oligonucleotides was investigated. siRNA and siRNA-L$_2$ showed resistance to degradation in serum over the pharmacokinetic time frame assessed, and L$_2$ modification imparted a slight improvement in resistance to serum degradation (FIG. 3E-F).

TABLE 1

Key pharmacokinetics parameters for siRNA-L$_2$ vs. siRNA

| Parameter | siRNA | siRNA-L$_2$ | P value |
|---|---|---|---|
| t1/2, circulation, min | 2.3 ± 0.2 | 13.1 ± 1.6 | 0.0023 |
| AUC$_{circ, 0-\infty}$, fluor. intensity × min | 5,500 ± 800 | 47,300 ± 6,700 | 0.0034 |
| Fraction kidney radiance | 0.790 ± 0.018 | 0.503 ± 0.014 | <0.0001 |

Figure 3G:
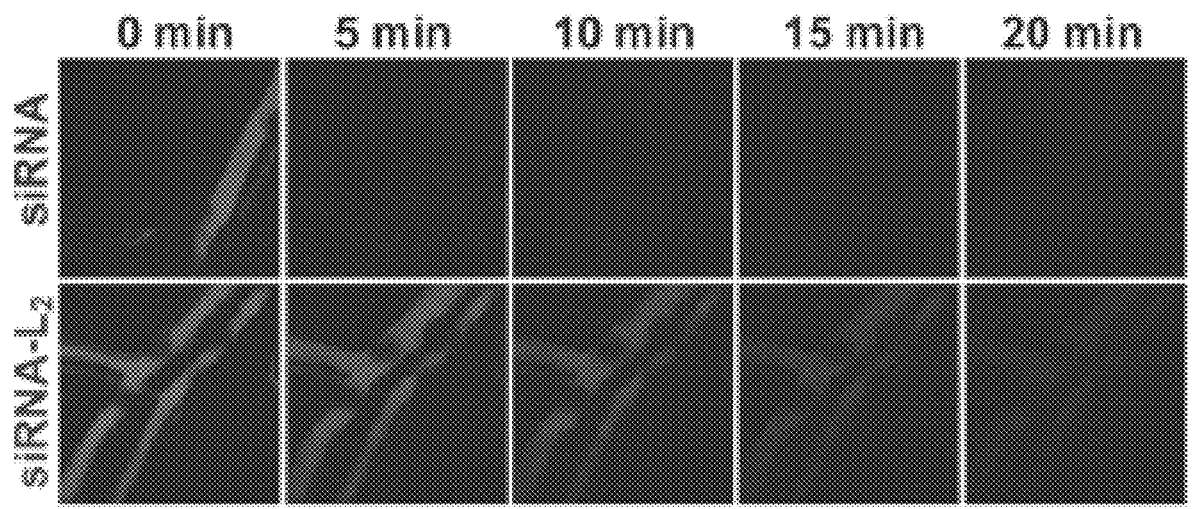
Figure 4A:
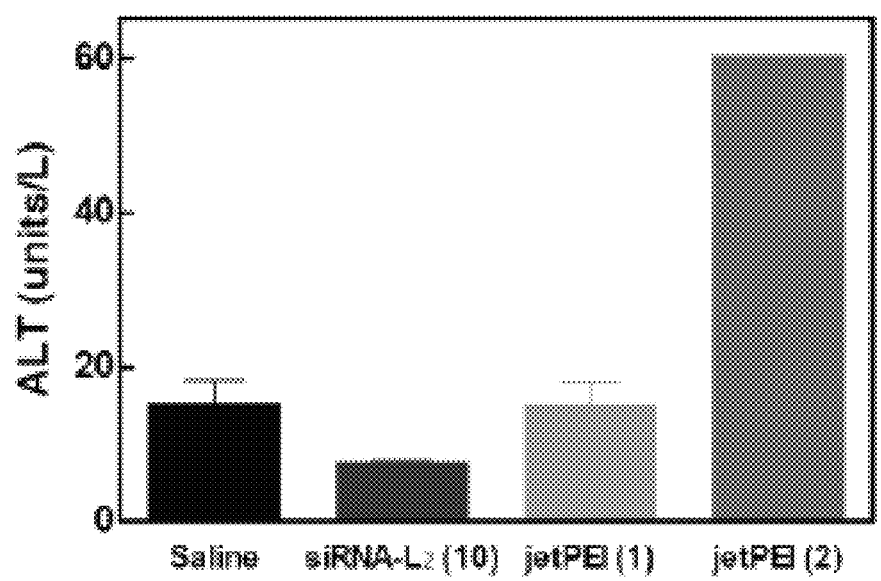
FIGS. 4A-E. Blood chemistry panel and body weight of mice injected with siRNA-L2 (10 mg/kg) or in vivo jetPEI loaded with siRNA (1 mg/kg, 2 mg/kg). (A) ALT: alanine aminotransferase; (B) AST: aspartate aminotransferase; (C) BUN: blood urea nitrogen; (D) Creatinine, (reading for in vivo jetPEI at 2 mg/kg was not measurable). (E) Body weight pre-injection (day 0) and 24 hours post-injection (day 1). n=4, standard error is plotted. 3 of 4 mice in the 2 mg/kg in vivo jetPEI did not survive treatment and could not be included in analysis.
Figure 4B:
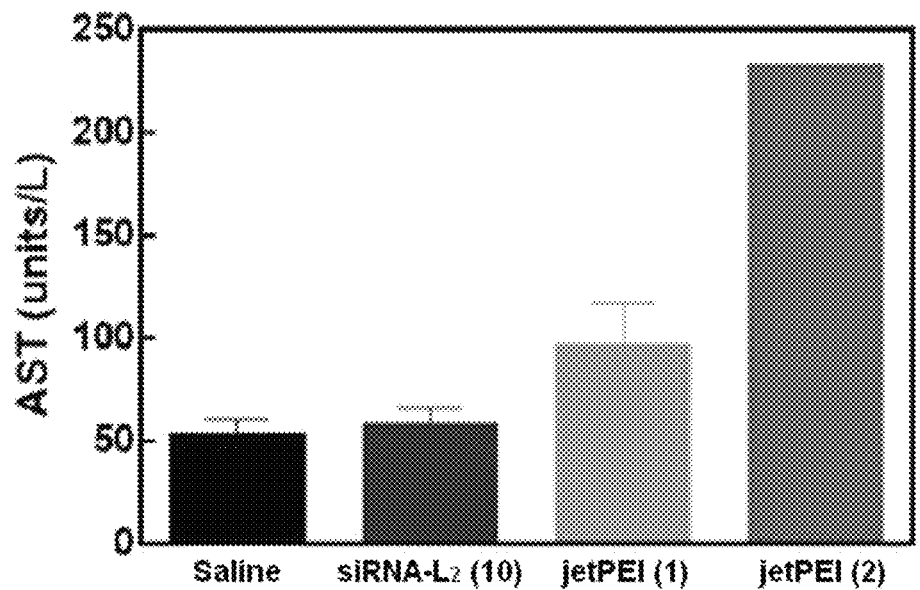
Figure 4C:
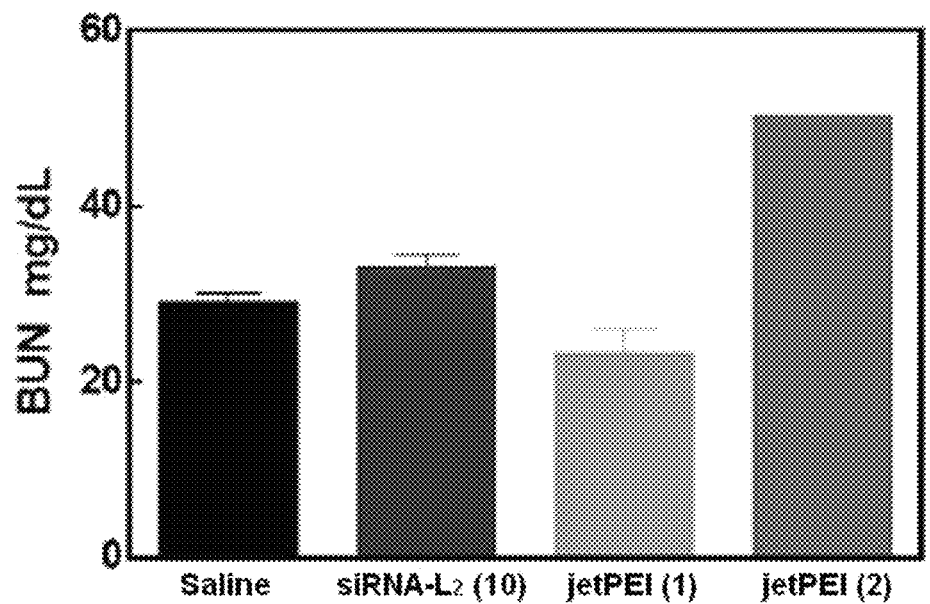
Figure 4D:
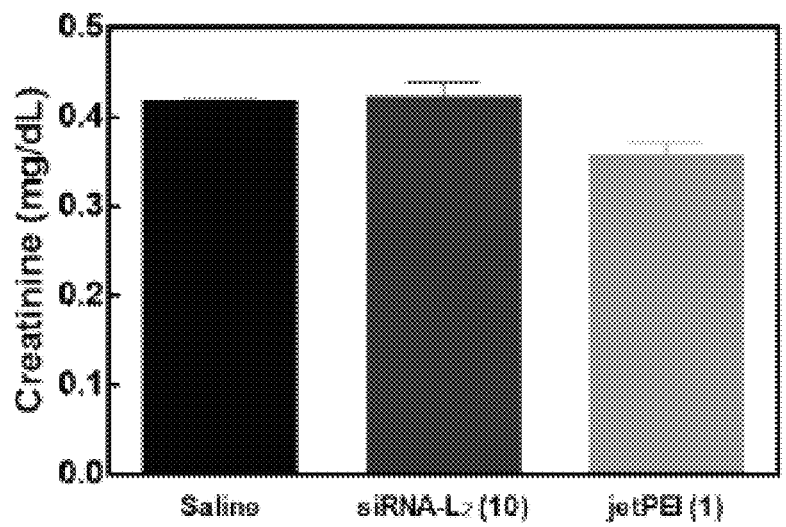
Figure 4E:
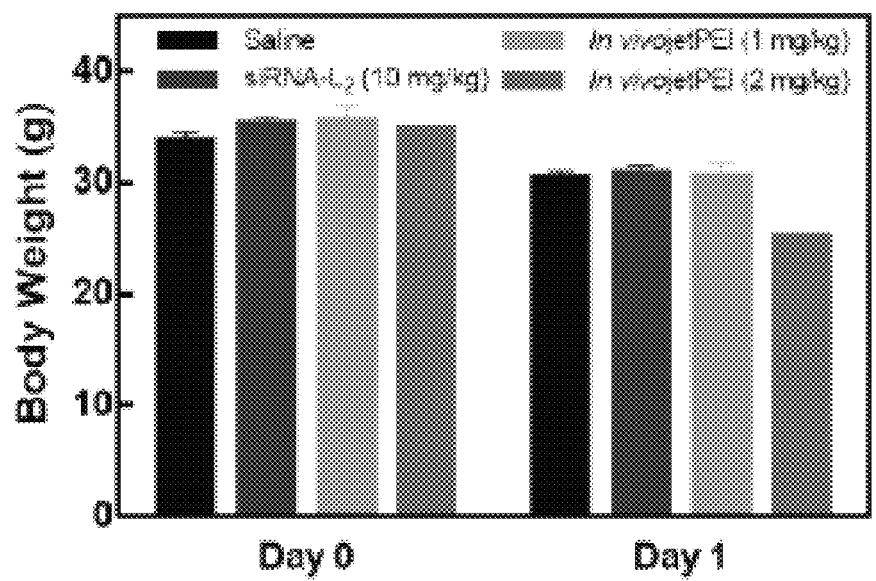

Biodistribution of siRNA vs. siRNA-L$_2$ was evaluated in excised organs at 20 min postinjection. For in vivo studies, siRNA-L$_2$ exhibited increased accumulation in almost all organs, likely due to its prolonged circulation time and reduced clearance into the urine in comparison with unmodified siRNA (FIG. 3G). The kidneys were the sole exception, showing significantly more unmodified siRNA accumulation (a 1.6-fold greater fraction of the total organ radiance) at this early time point. This illustrates that using albumin as a natural carrier for siRNA-L$_2$ allows reduction of acute clearance through the renal route.

siRNA-L$_2$ Outperforms a Leading in Vivo Nanoparticle Carrier in Safety and Tumor Accumulation. The reduction in kidney accumulation and prolonged circulation half-life of siRNA-L$_2$ motivated a comparison with commercially available in vivo nanoparticles. Of particular interest is the biodistribution profile of siRNA-L$_2$ in comparison with typical nanocarriers, as high uptake by mononuclear phagocytic system organs (the liver and the spleen) can result in minimal dose accumulation at the target site. Compared with nanoparticles, siRNA-L$_2$ is expected to avoid this off-target accumulation and to more readily penetrate tumor tissue.

siRNA-L$_2$ was compared with a leading formulation for nanoparticle-based in vivo nucleic acid delivery, in vivo jetPEI. In vivo jetPEI nanoparticles (jetPEI NPs) have been used in clinical trials, and this comparison is therefore a stringent test for therapeutic potential. Before in vivo biodistribution studies, tolerated doses were determined for siRNA-L$_2$ and jetPEI NPs. siRNA-L$_2$ is expected to avoid the toxic side effects associated with high doses of cationic nanocarriers, permitting safe use at higher dosages and potentially expanding the ultimate therapeutic index of siRNA drugs. Toxicity was investigated by monitoring mouse body weight and quantifying blood chemistry markers of liver [alanine aminotransferase (ALT) and aspartate aminotransferase (AST)] and kidney [blood urea nitrogen (BUN) and creatinine] toxicity. Mice injected with an siRNA-L$_2$ dose of 10 mg/kg exhibited normal ALT, AST, and BUN levels statistically equivalent to those of saline-injected mice; these mice also showed no change in body weight (FIGS. 4A-E). Delivery of jetPEI NPs at a dose of 1 mg/kg created no signs of toxicity, but doubling that dose to 2 mg/kg resulted in mortality for three of four mice and showed marked hepatic and renal toxicity in the single surviving mouse. These data suggest that siRNA-L$_2$ is a safer alternative to nanocarrier-based delivery with the potential for a much broader therapeutic index. The maximum tolerated dose (MTD) of 1 mg/kg for in vivo jetPEI and a well-tolerated dose of 10 mg/kg for siRNA-L$_2$ were used in subsequent studies (MTD not determined for siRNA-L$_2$).

Figure 5A:
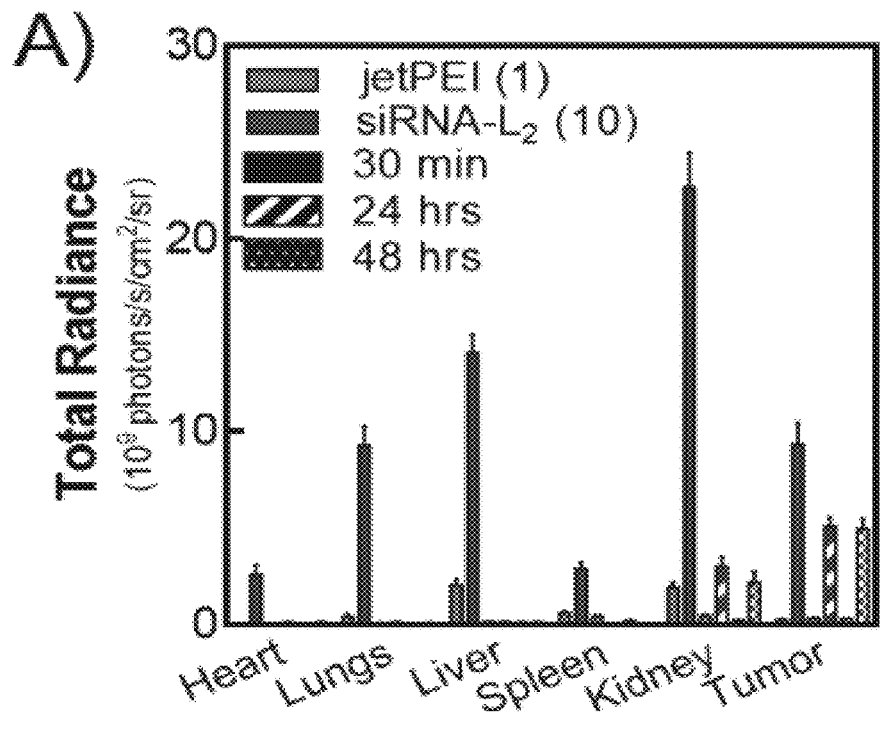
FIGS. 5A-H siRNA-$L_2$ achieves superior delivery to PDX and orthotopic tumors. Biodistribution was evaluated using a nontoxic dose of 1, 10 mg/kg of siRNA-$L_2$ and the MTD of 1 mg/kg jetPEI NPs. (A-F) Orthotopic model: (A) Absolute organ radiance for siRNA-L2 (10 mg/kg), jet PEI NPs (1 mg/kg). (B) Fraction organ radiance for siRNA-$L_2$, jetPEI NPs. (C) Absolute tumor radiance; exponential decay fits plotted. (D) Fraction tumor radiance; **P<0.01. (E) Tumor: liver ratio reveals a lower proportion in the liver for siRNA-L2 in comparison with jetPEI NPs. n=4, SE plotted. (F) Representative images depicting accumulation in liver, tumors. (G and H) PDX model: (G) Biodistribution and (H) plotted tumor radiance (n=2) of dose-matched jetPET NPs and siRNA-$L_2$ at 24 h. Radiance units are photons per FIG. 6. Representative images of biodistribution to the organs in orthotopic tumor-bearing mice. siRNA-L2 was evaluated at 1, 10 mg/kg and jetPEI NPs were evaluated at 1 mg/kg.
Figure 5B:
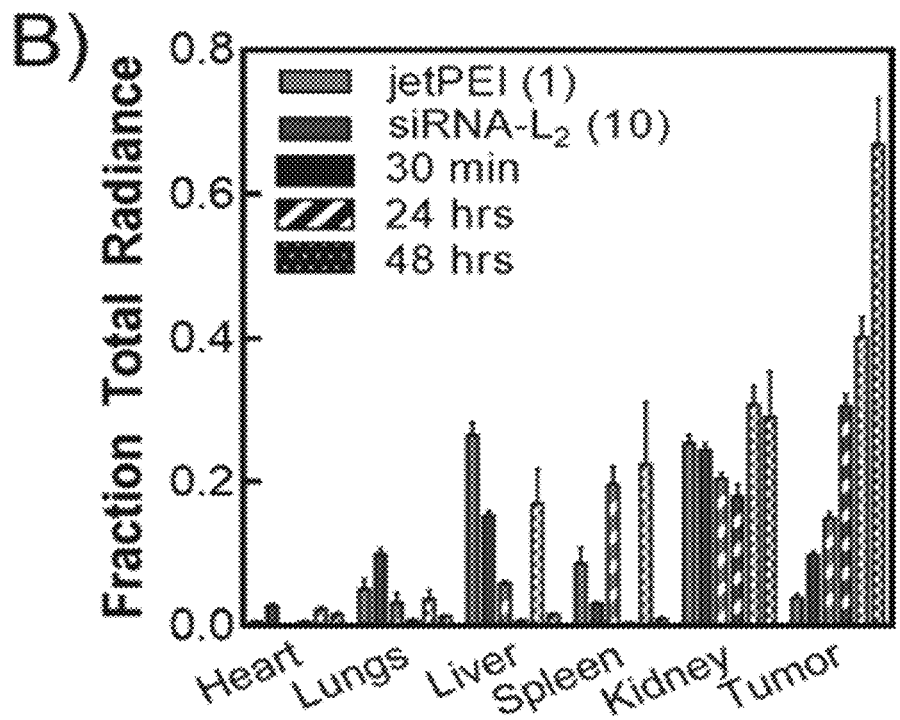
Figure 6:
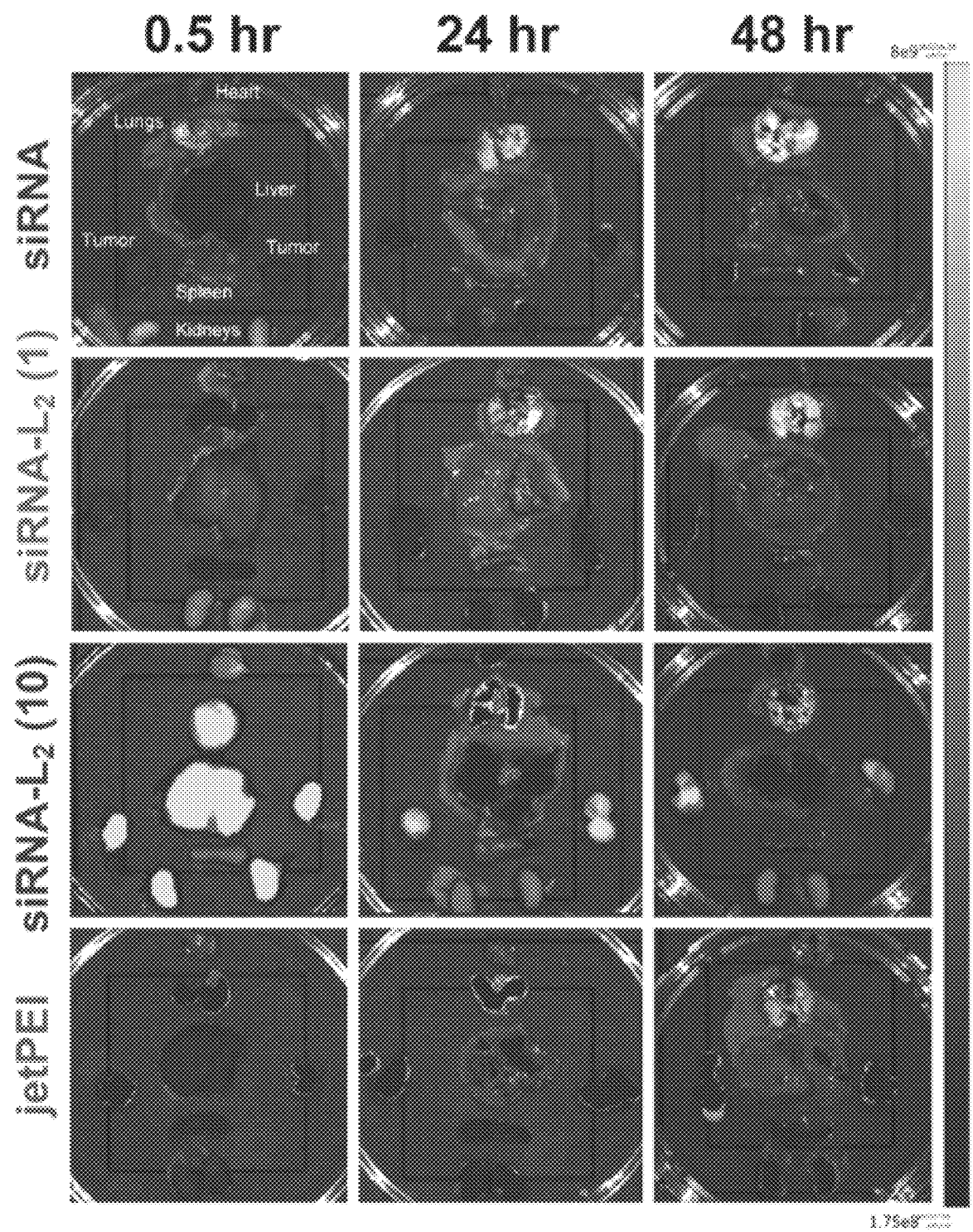
Figure 7A:
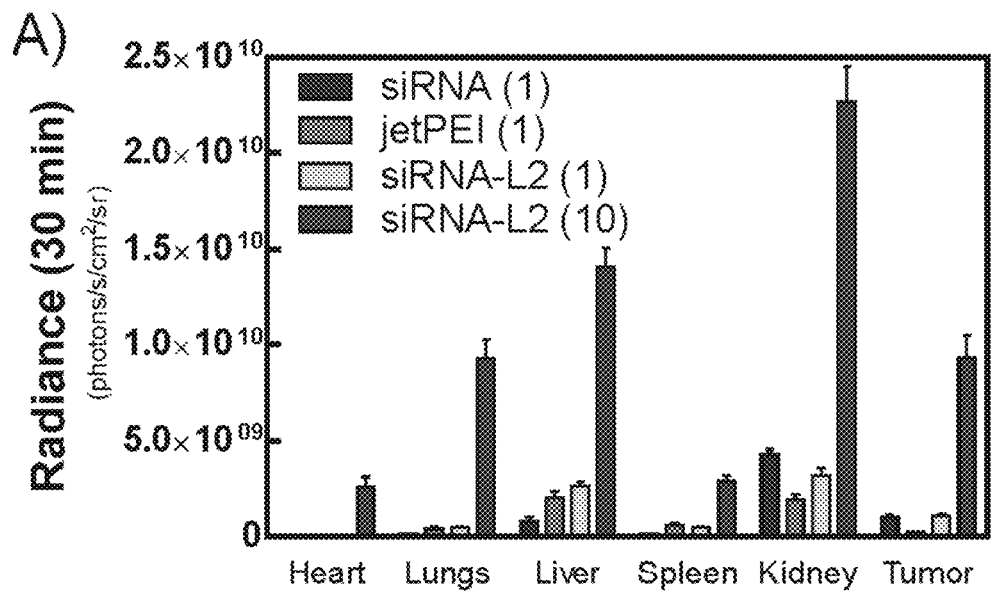
FIGS. 7A-F. In an orthotopic tumor model, absolute radiance per each organ at (A) 30 minutes, (B) 24 hours, (C) 48 hours and fraction of total radiance per each organ at (D) 30 minutes, (E) 24 hours, (F) 48 hours. n=4, standard error plotted.
Figure 7B:
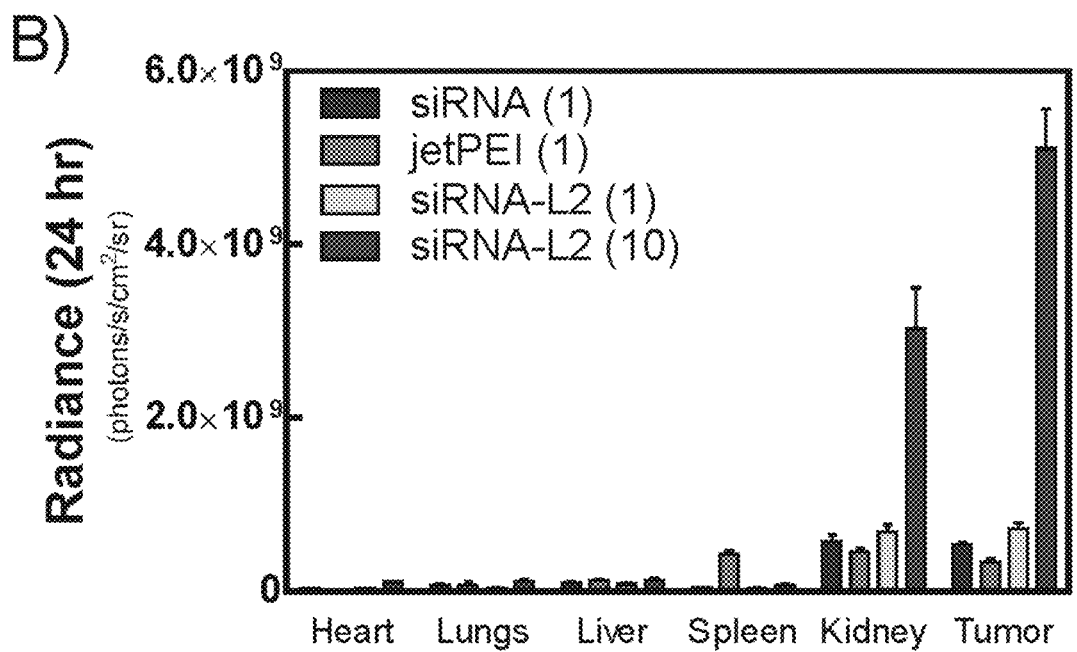
Figure 7C:
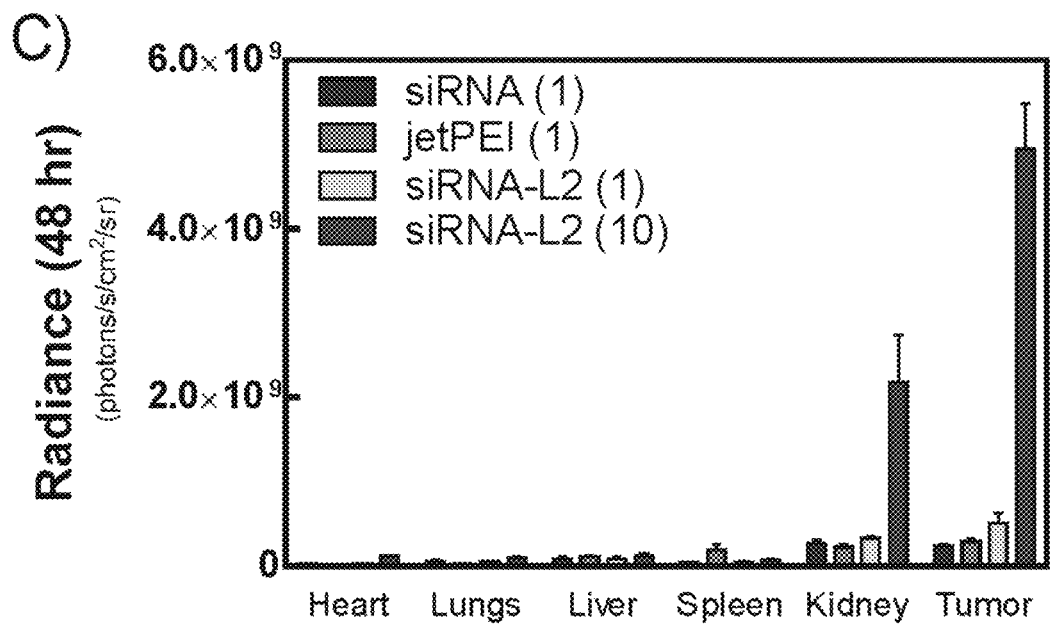
Figure 7D:
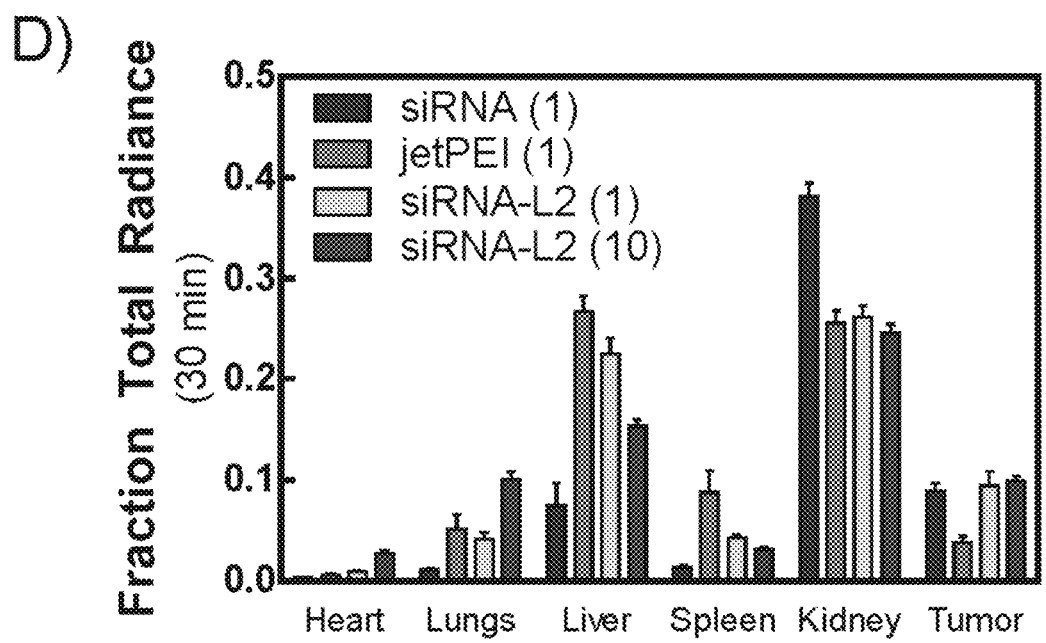
Figure 7E:
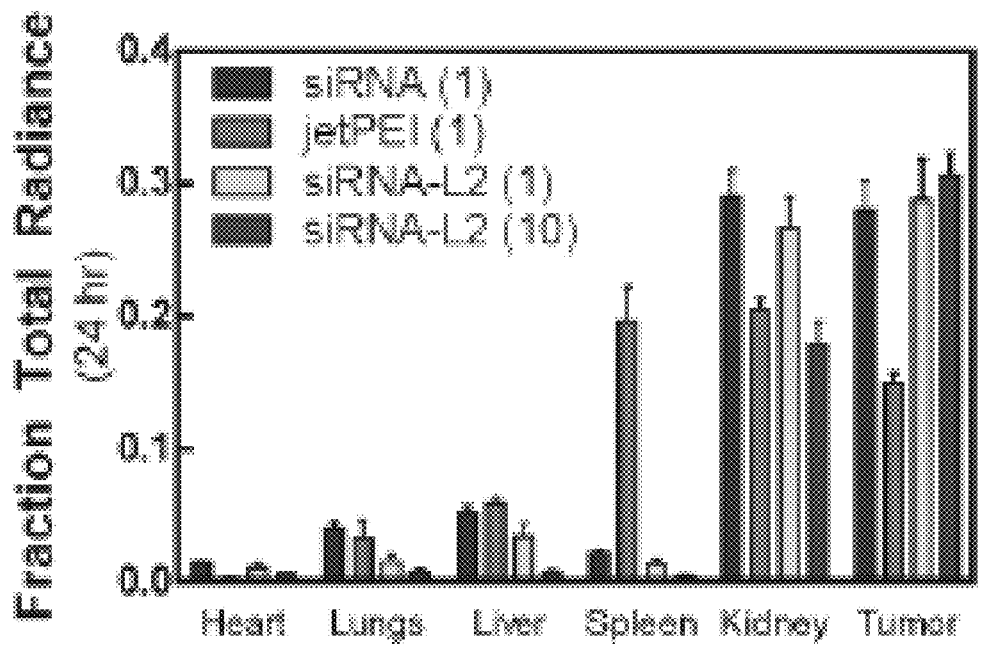
Figure 7F:
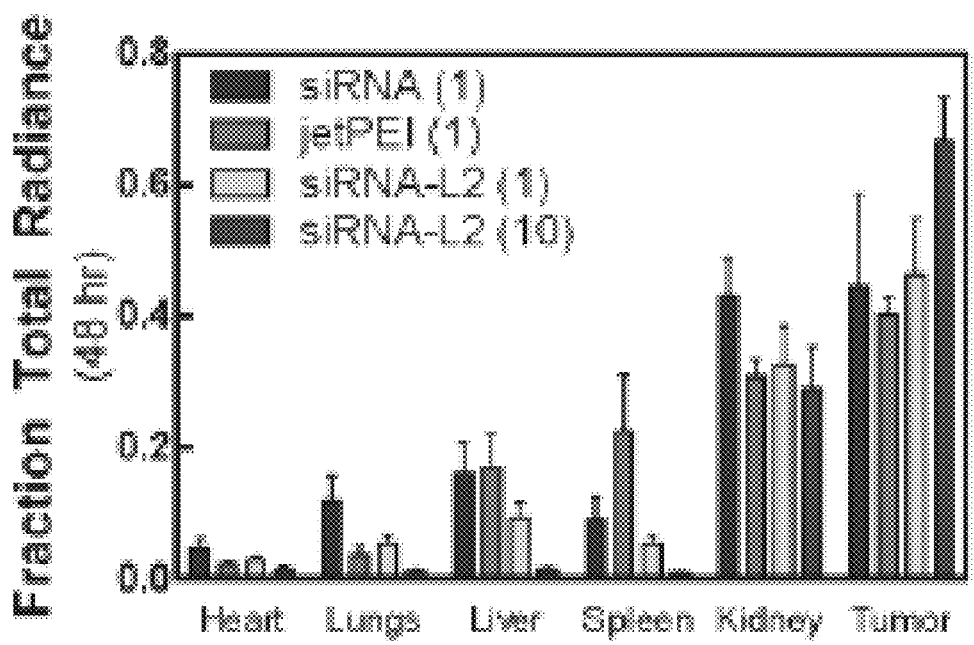

The biodistribution profile of the L$_2$ conjugate vs. jetPEI NPs was evaluated in a mouse orthotopic xenograft tumor model. siRNA-L$_2$ or jetPEI NPs were injected i.v. into tumor-bearing mice and organs were evaluated for siRNA accumulation. Comparing the absolute radiance in the organs over time from mice treated with jetPEI NPs or siRNA-L$_2$, it is evident that the 10-mg/kg treatment of siRNA-L$_2$ significantly enhances accumulation in all of the organs at an acute (30 min) time point (FIGS. 5A, 6, and 7A). Notably, the vast majority of siRNA-L$_2$ was cleared from all organs excepting the kidneys and tumors by 24 h (FIGS. 5A and 7A-F). jetPEI NPs, in contrast, create higher proportional delivery to and retention within the mononuclear phagocyte system (VIPS) clearance organs (the liver and spleen) (FIG. 5B).

Figure 5C:
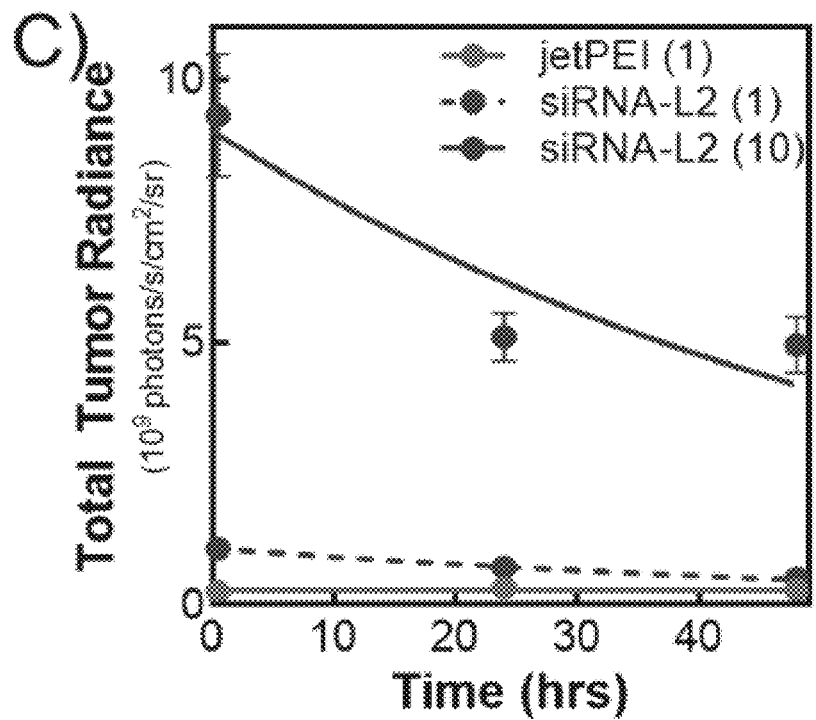
Figure 5D:
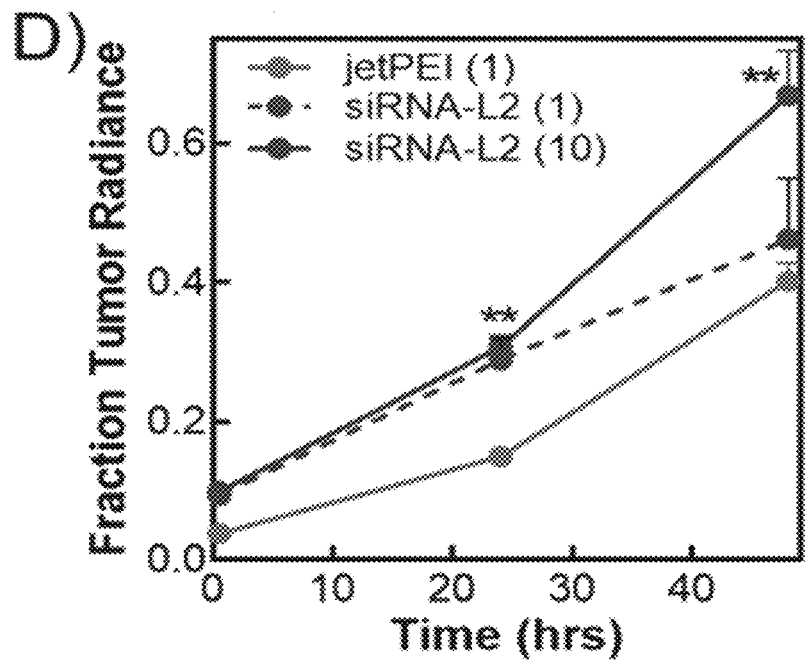

The in vivo tolerability of high siRNA-L$_2$ doses enables a remarkable increase in tumor accumulation (FIGS. 5C-D). The area under the curve within the tumor was 19.3-fold higher for siRNA-L$_2$ at 10 mg/kg than for the maximum tolerated dose of jetPEI NPs (Table 2). Dose-matched siRNA-L$_2$ at 1 mg/kg also outperforms jetPEI NPs in this measure of tumor accumulation by 2.4-fold. Additionally, the fraction of the total organ radiance in the tumors is consistently higher for siRNA-L$_2$ at both doses compared with jetPEI NPs, indicating more preferential tumor accumulation with siRNA-L$_2$ relative to jetPEI NPs.

TABLE 2

Key pharmacokinetic parameter comparisons of siRNA-L$_2$ vs. jetPEI NPs

| Parameter | jetPEI NPs | siRNA-L$_2$ (1) | siRNA-L2 (10) | P value$_{L2(1)}$ | P value$_{L2}$(10) |
|---|---|---|---|---|---|
| AUC$_{tumor, 0.5-48\,h}$, radiance × h | 1.48 × 10$^{10}$ | 3.61 × 10$^{10}$ | 2.90 × 10$^{11}$ | | |
| Liver:tumor ratio$_{24\,h,\,orthotopic}$ | 2.6 ± 0.2 | 15.4 ± 5.0 | 40.7 ± 5.2 | 0.1117 | 0.0007 |
| Liver:tumor ratio$_{24\,h,\,PDX}$ | 1.5 ± 0.4 | 7.8 ± 1.8 | | 0.1357 | |
| Liver:tumor ratio$_{48\,h,\,orthotopic}$ | 2.8 ± 0.2 | 6.2 ± 2.6 | 43.1 ± 2.7 | 0.1739 | 0.0007 |
| Fold tumor cell uptake, 30 min | 7.2 ± 0.6 | 34.7 ± 4.7 | 325.2 ± 29.0 | 0.0001 | <0.0001 |
| Fold tumor cell uptake, 24 h | 16.7 ± 1.0 | 31.0 ± 3.6 | 326.8 ± 16.0 | 0.0032 | <0.0001 |

Figure 5E:
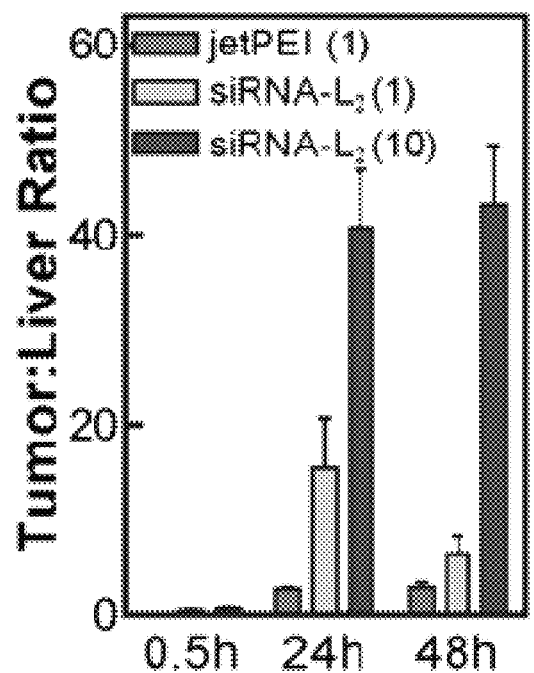
Figure 5F:
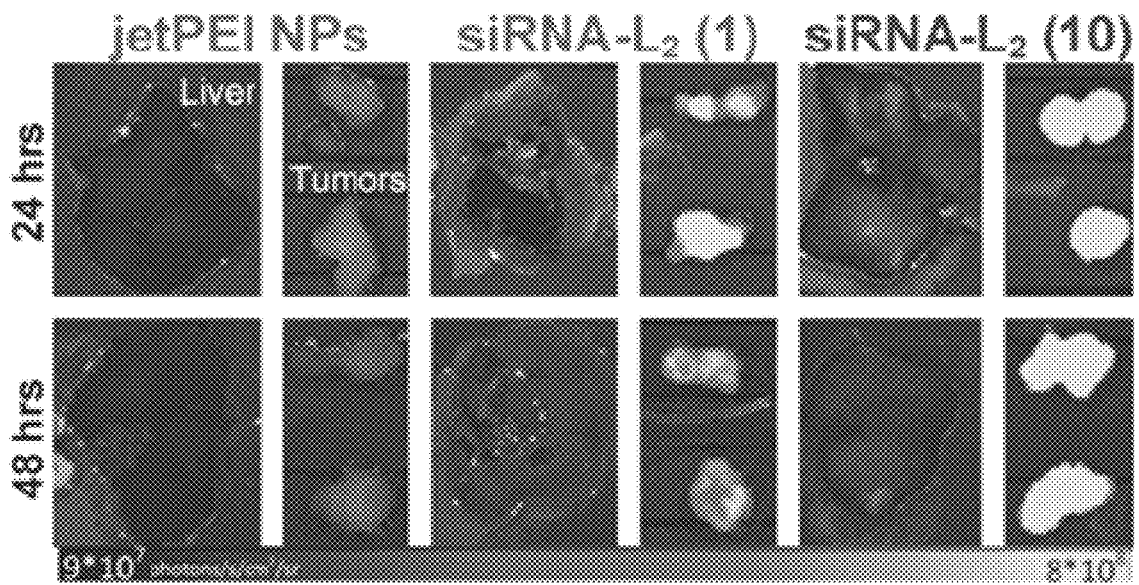

To further annotate the ability of siRNA-L$_2$ to avoid the typical MPS organ accumulation of nanoparticles and accumulate preferentially within tumors, we evaluated the tumor: liver radiance ratio. At the 10-mg/kg siRNA-L$_2$ dose, a tumor:liver accumulation of more than 40:1 was observed at both 24 and 48 h, indicating successful accumulation at a nonhepatic site (FIGS. 5E-F and Table 2). In contrast, jetPEI NPs displayed a tumor:liver ratio of below 3:1, a more than 15-fold decrease compared with siRNA-L$_2$ at 10 mg/kg and also lower than that observed for siRNA-L$_2$ at 1 mg/kg (which achieved a tumor:liver ratio of ~15:1).

Figure 5G:
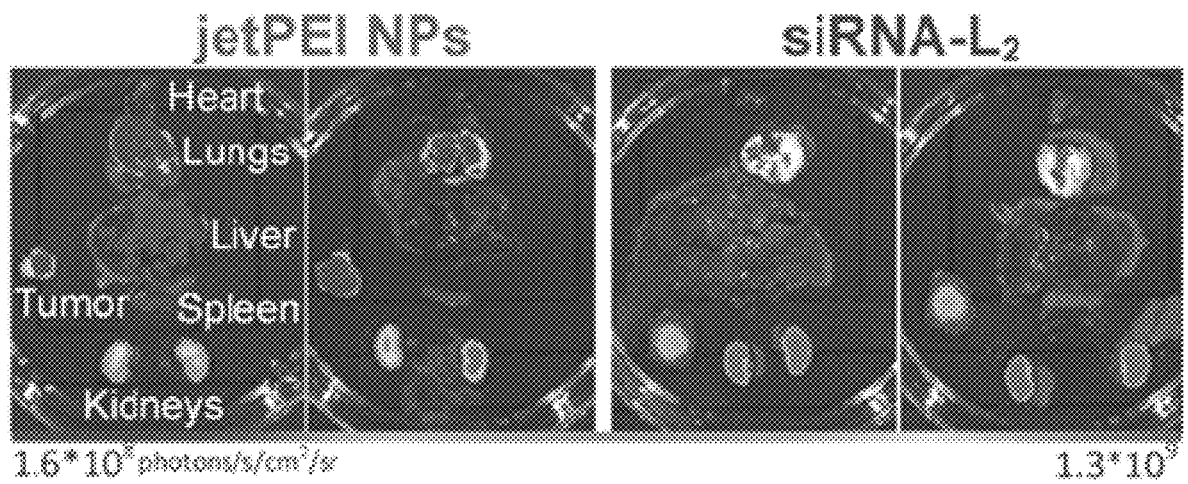
Figure 5H:
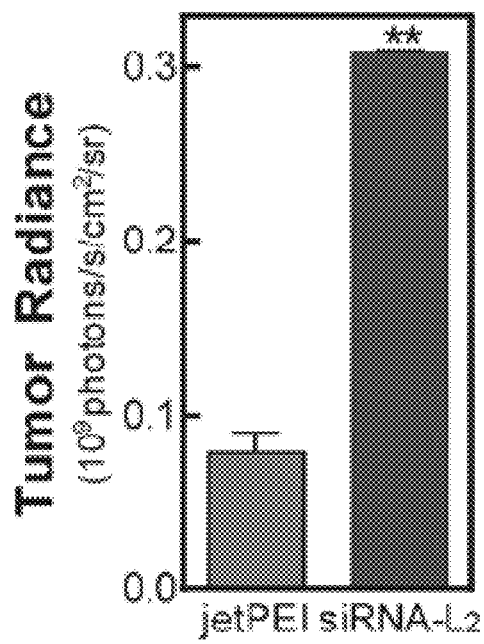
Figure 8A:
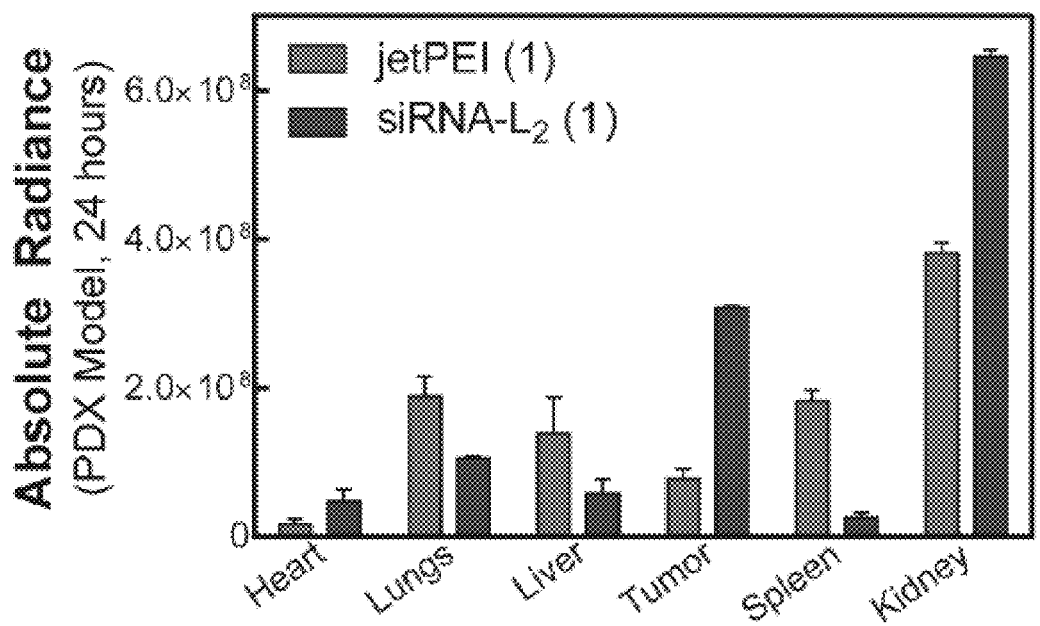
FIGS. 8A-B. In a PDX tumor model, (A) absolute radiance per each organ at 24 hours and (B) tumor:liver ratio of jetPEI NPs and siRNA-L2 in a PDX tumor model after intravenous injection at 1 mg/kg. n=2, standard error plotted.
Figure 8B:
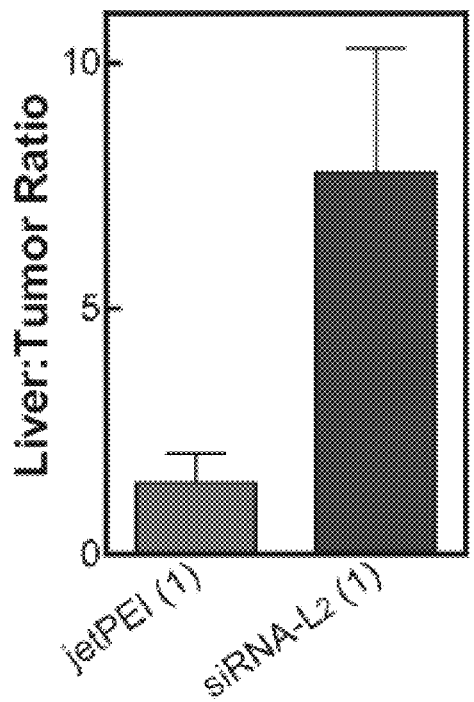
Figure 9A:
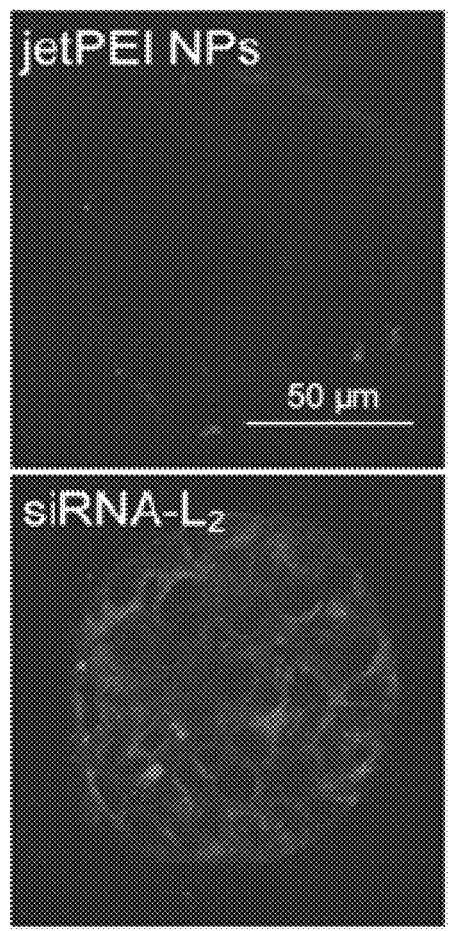
FIGS. 9A-D. siRNA-L2 penetrates tumors and is internalized by tumor cells, resulting in sustained gene silencing in a mouse tumor model. (A) Representative confocal microscopy images of tumor spheroid penetration and internalization. (B) Cellular internalization of Cy5-labeled siRNA-L2 or jetPEINPs loaded with Cy5 siRNA in MCF-7 tumor spheroids, normalized to no treatment. Treatment at 100 nM, quantified by flow cytometry; n=3, SE plotted, ***P<0.001. (C) Cellular internalization in tumor cells isolated from orthotopic xe-nograft mouse tumors after injection of jetPEI NPs at 1 mg/kg or siRNA-L2 at 1, 10 mg/kg, normalized to no treatment; n=6-8 tumors. (D) Gene silencing of luciferase-targeted siRNA-L2 compared with unmodified siRNA in an ortho-topic xenograft mouse tumor model; treatment at day 0 and 1 (as indicated by arrows) at 10 mg/kg, n=10. *P<0.05, **P<0.01: luc-L2 vs. scr-$L_2$, †P<0.05, ‡P<0.01: luc-L2 vs. luc. SE plotted.
Figure 9B:
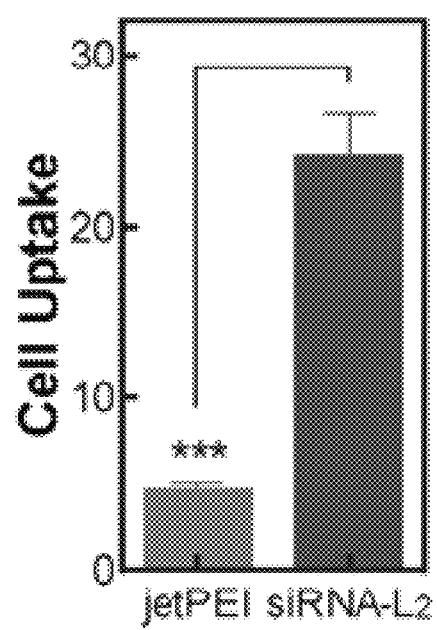
Figure 10A:
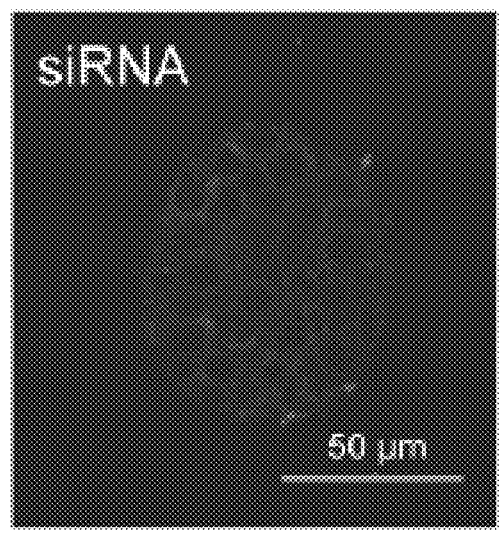
FIGS. 10A-E. (A) Representative image of tumor spheroid uptake for siRNA. (B) Cellular uptake, as evaluated by flow cytometry, of MCF-7 breast cancer cells grown in tumor spheroids. Data are expressed as fold increase in fluorescence relative to untreated cells. Treatment with in vivo jetPEI complexes resulted in significantly less uptake than siRNA, while siRNA-L2 achieved the highest uptake. (C) Percentage positive cells, as evaluated by flow cytometry, of MCF-7 breast cancer cells grown in tumor spheroids. Treatment with in vivo jetPEI complexes resulted in significantly fewer positive cells than siRNA and siRNA-L2, consistent with its poor penetration into the interior of the tumor spheroids. (D) Representative histograms of flow cytometric evaluation of Cy5-labeled siRNA uptake by MCF-7 breast cancer cells grown in tumor spheroids. (E) Percentage cy5 siRNA positive tumor cells isolated from orthotopic xenograft mouse tumors. n=6 to 8. n=3, standard error plotted; =p<0.01, *=p<0.001.
Figure 10B:
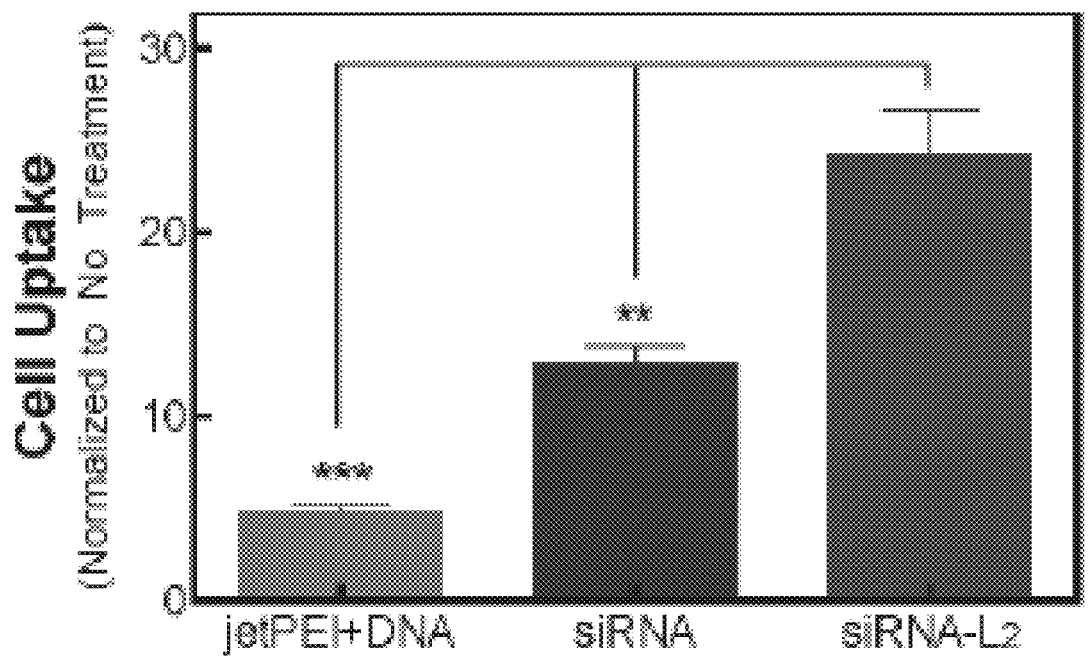
Figure 10C:
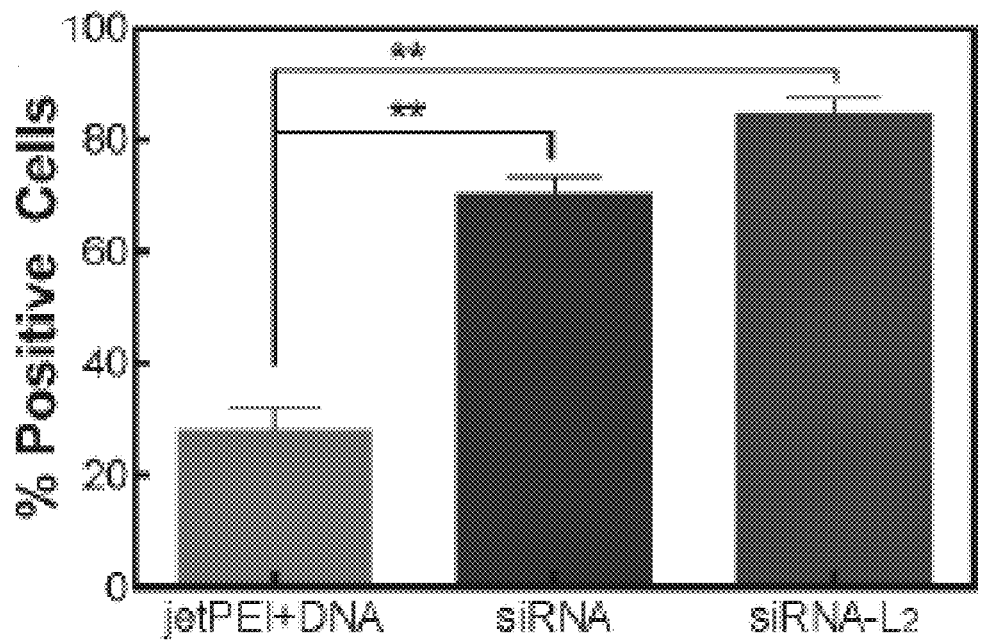
Figure 10D:
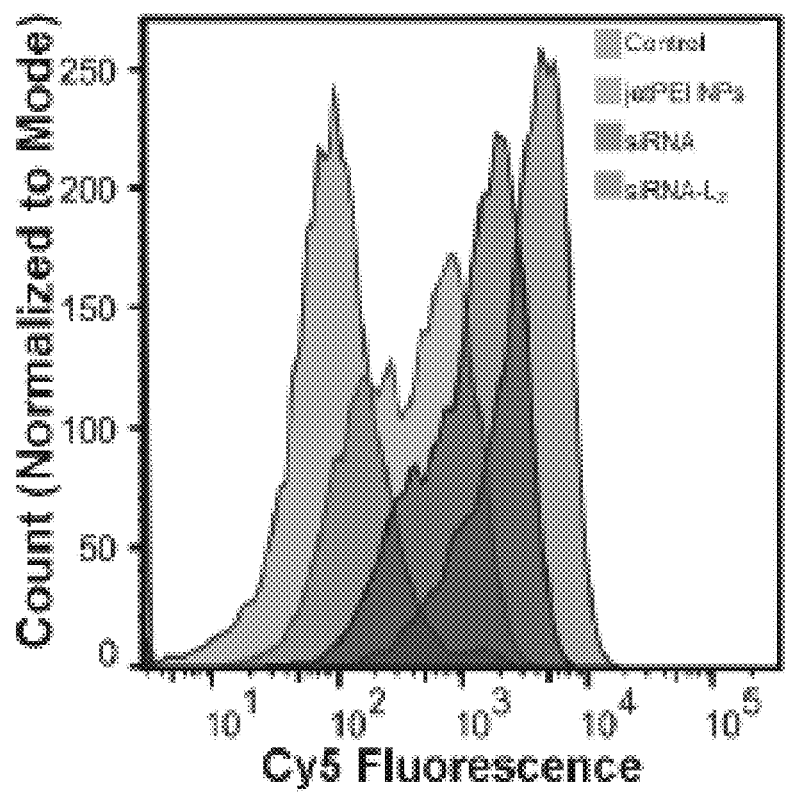

The clear superiority of siRNA-L$_2$ in the orthotopic model motivated investigation in a more clinically relevant patient-derived xenograft (PDX) model of triple-negative breast cancer. Dose-matched siRNA-L$_2$ and in vivo jetPEI NPs at 1 mg/kg were injected i.v. and biodistribution was evaluated at 24 h. siRNA-L$_2$ attained 4.0-fold greater tumor distribution in the PDX model than jetPEI NPs (whereas there was a 2.2-fold increased tumor delivery in the dose-matched orthotopic model) at 24 h (FIGS. 5G-H and 8A). Compared with the orthotopic model, achieving tumor accumulation in the PDX model was more challenging. The added challenge of PDX tumors was more detrimental for the tumor delivery with jetPEI NPs than siRNA-L$_2$. Total tumor accumulation in PDX tumors was 4.3-fold lower than orthotopic tumors for jetPEI NPs whereas it was only reduced by 2.4 fold for siRNA-L$_2$. The lower NIPS accumulation of siRNA-L$_2$ relative to NPs was consistent in the PDX model, with siRNA-L$_2$ again showing a marked improvement in tumor: liver ratio (8:1 vs. 1:1) (FIG. 8B).

siRNA-L$_2$ Exhibits Homogeneous Distribution and High Cellular Internalization at the Tumor Site. The small size of albumin-bound siRNA-L$_2$ is expected to increase tissue penetration and homogeneity of distribution over nanoparticles. Using an in vitro tumor spheroid model, the penetration and distribution of siRNA-L$_2$ vs. jetPEI NPs throughout 3D tumor architecture was evaluated. The siRNA-L$_2$ showed homogeneous and substantial cell uptake throughout the entirety of spheroids, whereas jetPEI NPs remained localized largely around the edges of the spheroid (FIG. 9A). Unmodified siRNA showed improved penetration into the interstitial spaces compared with the jetPEI complexes, but exhibited lower overall fluorescence than siRNA-L$_2$ (FIG. 10A). To complement these results, flow cytometry was used to measure uptake per cell (as quantified by mean intracellular fluorescence) in tumor spheroids that were dissociated and analyzed following siRNA formulation treatment. The cellular internalization of siRNA-L$_2$ was twofold higher than that of unmodified siRNA, evidencing an uptake benefit derived from hydrophobic modification (FIG. 10B). Compared with jetPEI NPs, siRNA-L$_2$ exhibited a greater than fivefold uptake increase (FIG. 9B), with 84% of siRNA-L$_2$-treated cells positive for uptake compared with 27% of jetPEI-NP-treated cells (FIGS. 10C-D).

Figure 9C:
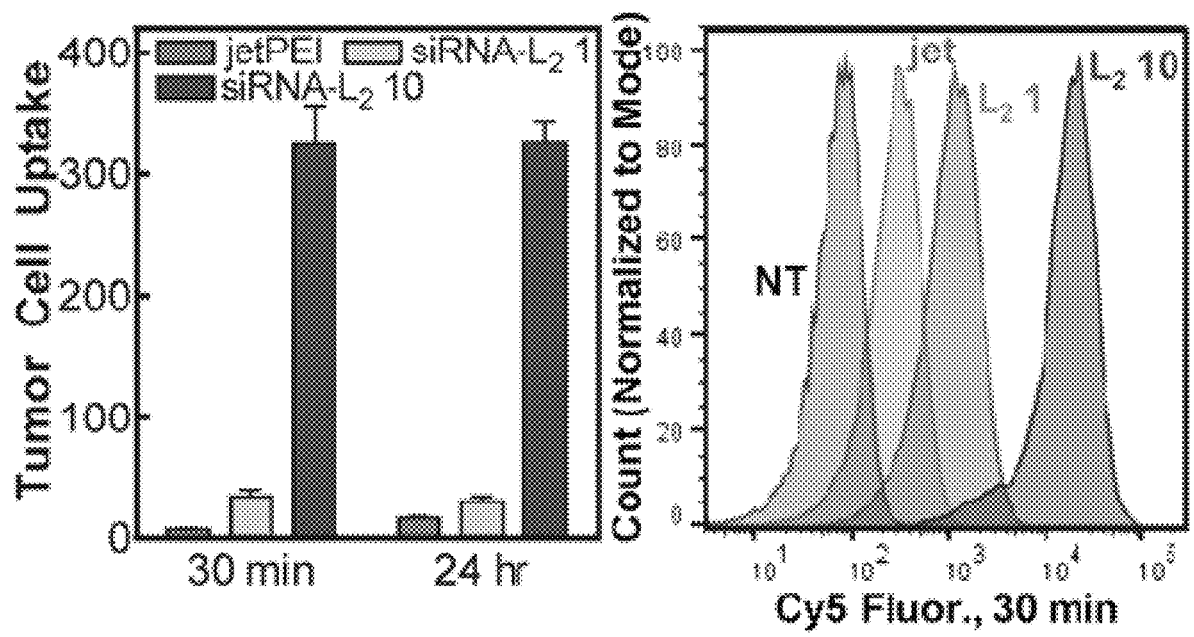
Figure 9D:
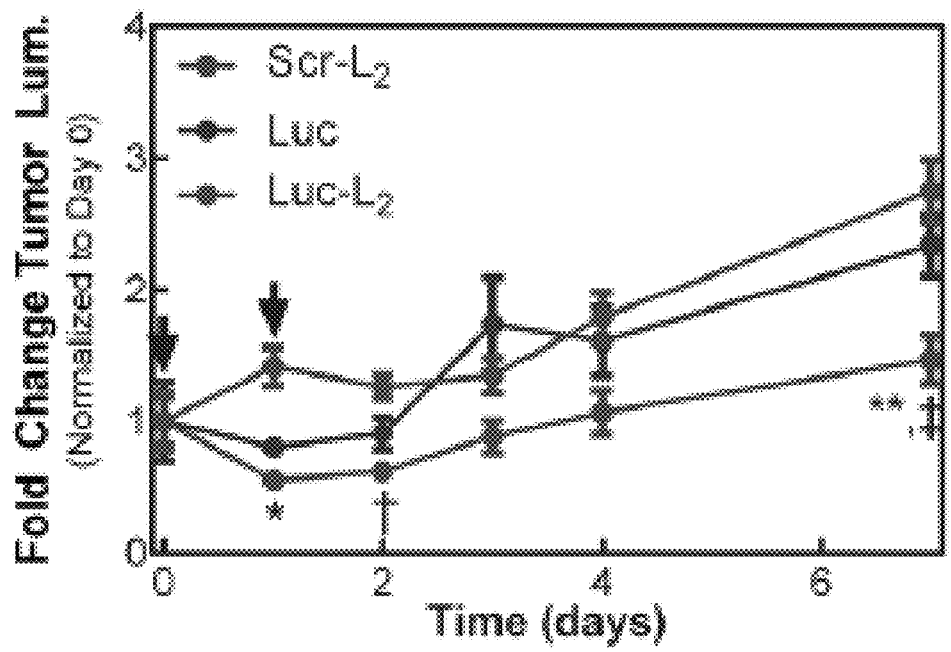
Figure 10E:
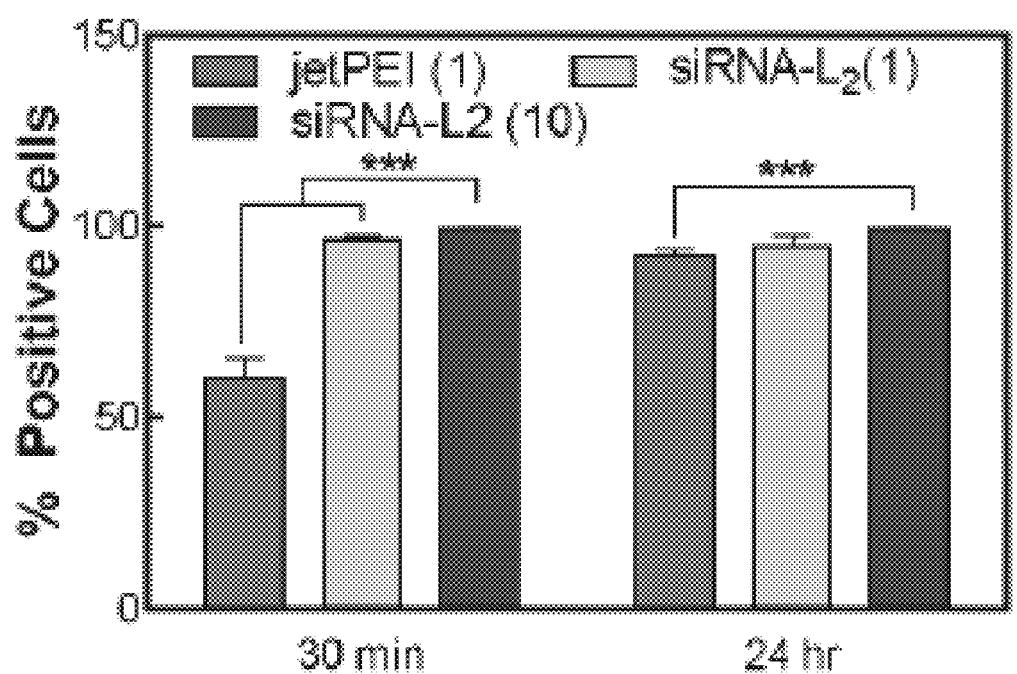
Figure 11A:
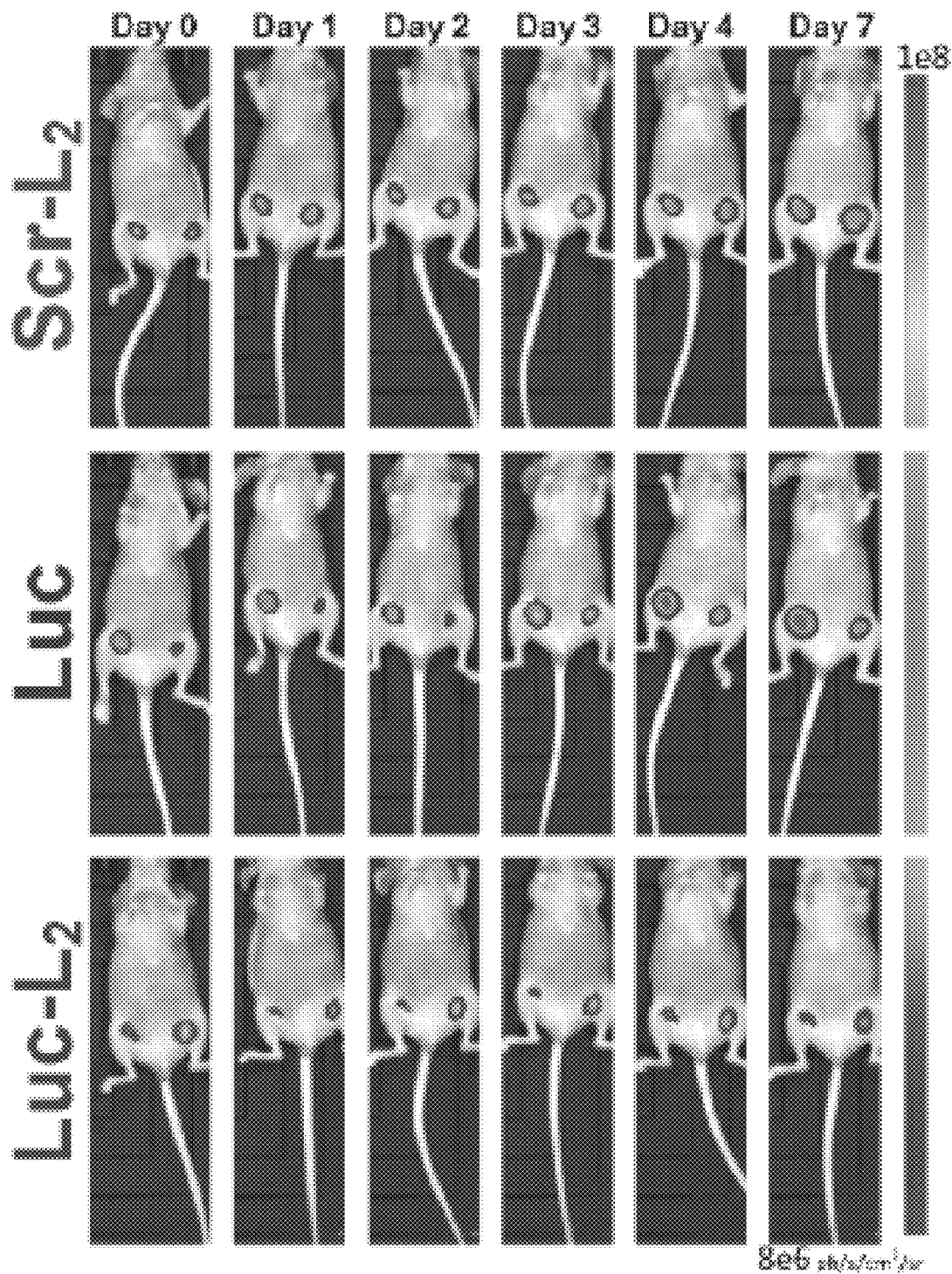
FIGS. 11A-D. (A) Representative images of tumor luminescence in mice with orthotopic luciferase-expressing tumors, treated with luc-L2, luc, or scr-L2 at 10 mg/kg on day 0 and 1. (B) Gene silencing jetPEI NPs complexed with luc compared to scr siRNA in an orthotopic xenograft mouse tumor model; treatment at day 0 and 1 (as indicated by arrows) at 1 mg/kg, n of 8; *=p<0.05. (C) Mouse body weight after treatment with luc-L2, luc, or scr-L2 at 10 mg/kg on day 0 and 1; body weight is consistent across treatment groups over the course of the experiment. n=5. (D) Mouse body weight after treatment jetPEI NPs complexed with luc or scr siRNA at 1 mg/kg on day 0 and 1; body weight is consistent across treatment groups over the course of the experiment. n=5. Standard error is plotted for all.
Figure 11B:
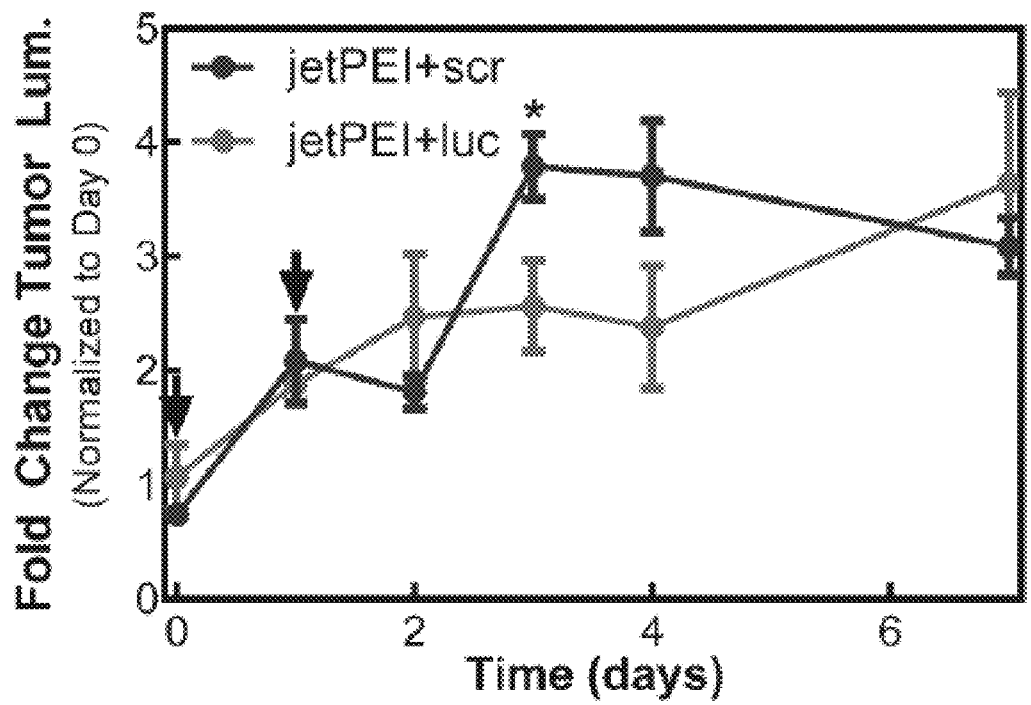
Figure 11C:
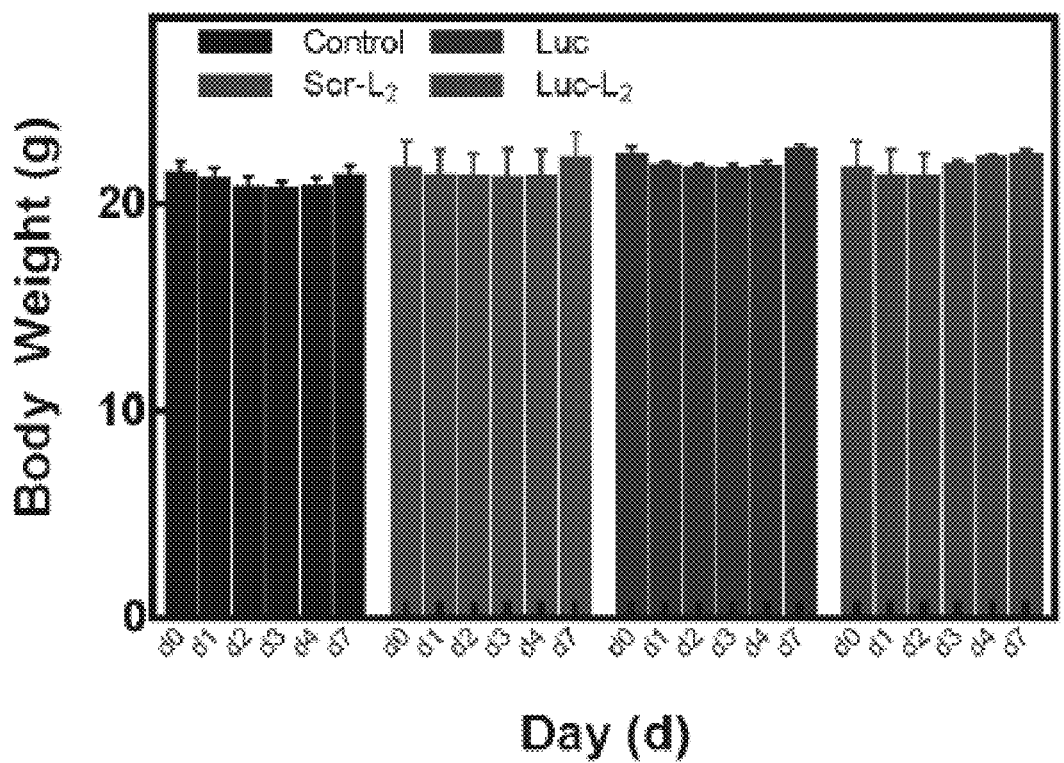
Figure 11D:
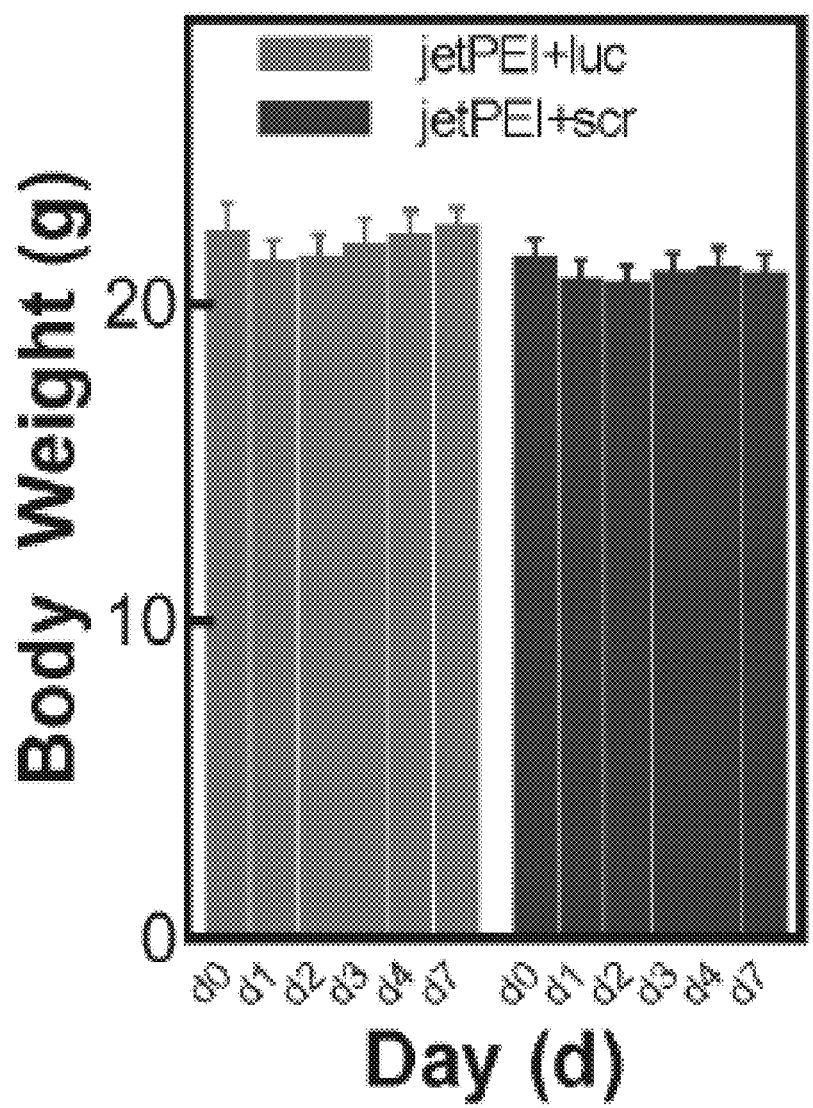

These in vitro tumor spheroid results inspired an investigation of tumor penetration and homogeneity of internalization by cells within orthotopic breast tumors in vivo. Following i.v. injection of siRNA-L$_2$ or jetPEI NPs, cells were isolated from excised tumors and evaluated by flow cytometry for cellular internalization. Tumor cells were identified by expression of green fluorescent protein (GFP). siRNA-L$_2$ outperformed jetPEI NPs at both 30 min and 24 h, with siRNA-L$_2$ at 1 mg/kg displaying 5- and 2-fold increased uptake at respective time points and siRNA-L$_2$ at 10 mg/kg showing 45- and 20-fold increased uptake (FIGS. 9C-D and Table 2). At 30 min, mice treated with siRNA-L$_2$ at either dose displayed uptake in more than 96% of tumor cells, whereas jetPEI-NP-treated mice showed uptake in only 60% of cells (FIG. 10E). The preferential and homogeneous distribution of siRNA-L$_2$ to tumor sites and high uptake by tumor cells makes it ideally suited for cancer therapies.

siRNA-L$_2$ Elicits Sustained Silencing in an in Vivo Tumor Model. The promising tumor penetration characteristics of siRNA-L$_2$ inspired examination of its gene silencing efficacy in vivo in an orthotopic mouse tumor model. After treatment with luciferase-targeted siRNA or siRNA-L$_2$ at days 0 and 1, luminescence was evaluated over 7 d, where an increase in luminescence indicates tumor growth and successful luciferase silencing abrogates the increase in luminescent signal. siRNA-L$_2$-treated tumors exhibited significantly reduced tumor luminescence in comparison with tumors treated with unmodified luciferase-targeting siRNA or inactive, control siRNA-L$_2$ sequences (FIG. 9D and FIG. 11A). Comparing to the scrambled siRNA-L$_2$ control, maximum silencing was more than 60% at day 1, with nearly 50% silencing sustained at day 7, revealing the prolonged gene silencing capacity of siRNA-L$_2$. Treatment with jetPEI NPs at a dose of 1 mg/kg elicited significant (~30%) silencing at day 3, but silencing was fully abrogated by day 7 (FIG. 11B). No change in mouse body weight was observed over the course of treatment, further indicating that siRNA-$L_2$ treatment is well-tolerated (FIGS. 11C-D).

Figure 12A:
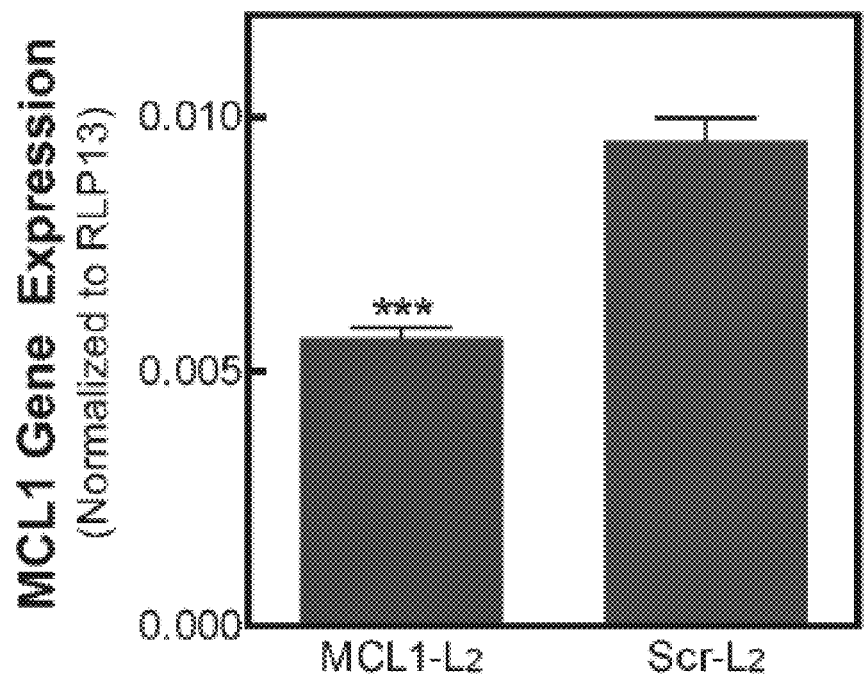
FIGS. 12A-B. siRNA-L2 (A) silences therapeutic gene MCL-1 and (B) increases caspase activity in vitro. Treatment of MCF-7 cells at 200 nM for 24 hours in 10% serum; n=3, standard error plotted. *** p<0.01.
Figure 12B:
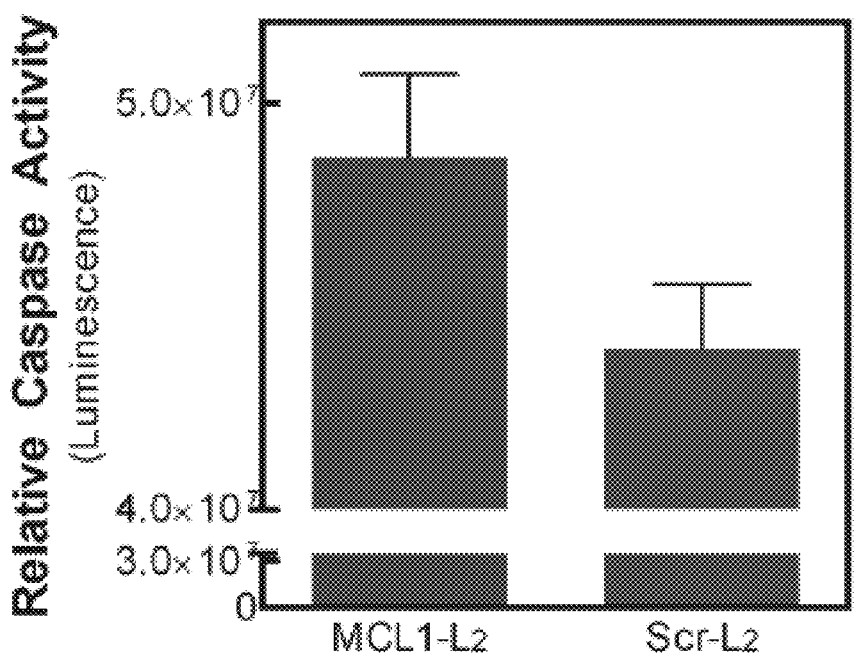

As an initial proof-of-concept of activity against a therapeutically 2Q:17 relevant gene, siRNA-$L_2$ that targets the negative regulator of apoptosis, myeloid leukemia cell differentiation protein (MCL-1), was synthesized. The siRNA-$L_2$ against MCL-1 achieved significant gene silencing in vitro at a reasonably low, 200-nM dose, and MCL-1 silencing correlated with a trend of functional increase in caspase activity (FIGS. 12A-B).

Discussion

Simple conjugation of a hydrophobic albumin-binding diacyl lipid moiety to siRNA is a powerful delivery strategy to improve siRNA pharmacokinetic properties. $L_2$ conjugation increases circulation half-life, cellular internalization capacity, and tumor penetration and retention of siRNA while simultaneously reducing accumulation in clearance organs. These myriad benefits lead to enhanced and prolonged in vivo gene silencing in tumors, supporting siRNA-$L_2$ as a potential cancer therapy that can act on currently undruggable targets.

Leveraging albumin as an endogenous nanocarrier is a relatively recent but extremely promising strategy to extend the circulation persistence of therapeutics. Clinically relevant examples range from Abraxane, an albumin-based nanoparticle that encapsulates Taxol, to Levemir, a therapeutic peptide modified to associate noncovalently with endogenous albumin. siRNA, with its high potential medical impact but characteristically short circulation half-life, is an ideal candidate to develop with albumin as an in vivo chaperone. Inducing high-affinity binding of siRNA to albumin via modification with a lipidic moiety is a logical strategy. Previous work has shown siRNA amenable to lipid modifications, which often confer improvements in nuclease resistance and cellular internalization without impacting gene silencing. Conjugation with $L_2$ therefore has potential benefits on enhancing molecule stability and uptake whereas also prompting in situ albumin binding. Notably, this binding is noncovalent and dynamic. In its physiological role as a fatty acid carrier, albumin facilitates the cellular uptake of lipids, likely through a variety of mechanisms that use receptors for both albumin and lipid domains. Conjugation of $L_2$ could allow siRNA-$L_2$ to hijack these natural pathways. Additionally, the hydrophobic interaction of the $L_2$ moiety with the cellular membrane could encourage siRNA-$L_2$ to be internalized independent of albumin.

$L_2$ modification as an albumin targeting approach is desirable for achieving pharmacokinetic improvements while maintaining simplicity and safety. Despite the synthetic complexity of nano-particle systems, siRNA-$L_2$ possesses a circulation half-life above that of non-cross-linked polyion nanoparticles and nearly equivalent to that observed in a relatively intricate cross-linked micelle system using cholesterol-modified siRNA. Perhaps more striking is the complete lack of toxicity observed for siRNA-$L_2$ at doses of 10 mg/kg, which sharply contrasts with the reported toxicity and immunogenicity of nanoparticulate carriers and our direct evaluation of in vivo jetPEI. siRNA-$L_2$ couples an improved circulation half-life with a lack of dose-limiting side effects, and therefore is anticipated to enable very broad therapeutic windows when developed against specific targets. Our demonstration of MCL-1 gene silencing and its link to caspase induction demonstrates the applicability of siRNA-$L_2$ to such therapeutic targets. Additionally, we expect that the efficacy of siRNA-$L_2$ could be further optimized through modifications to enhance in vivo stability and through identification of siRNA sequences with extremely potent silencing.

Another associated challenge with nanoparticle delivery systems is their preferential accumulation within clearance organs, specifically the liver and spleen. Accumulation of synthetic and toxic/immunogenic nanoparticle components in these organs is the typical cause of dose-limiting toxicities. However, siRNA-$L_2$ avoids capture in the MPS organs, which is characteristic of nanoparticles, while also exhibiting a significant reduction in the rapid renal clearance associated with unmodified siRNA delivery. This is exemplified by the tumor:liver accumulation ratio of more than 40:1 achieved by siRNA-$L_2$. The disparity between in vivo jetPEI, with a ratio of less than 3:1, is pronounced. The lack of siRNA-$L_2$ retention in the liver is a key advantage over nanoparticulate delivery systems and will allow a greater percentage of the injected dose to be retained at its site of action in tumors. The lower tumor:liver ratio observed with in vivo jetPEI and nanoparticle systems in the literature is consistent with reported challenges in achieving efficient nanoparticle delivery to tumor sites; in a comprehensive analysis of nanoparticle delivery to solid tumors, the median injected dose delivered to the tumor site was 0.7%. It is notable that even in recent, advanced, and promising nanoparticle systems, including those that use modifications for "stealth" or targeting mechanisms, the ratio of tumor:liver accumulation is consistently close to or below 1:1. The marked improvement of siRNA-$L_2$ in relative tumor accumulation supports its translational promise.

There is also a significant tumor penetration benefit of siRNA-$L_2$ due to its small size relative to nanoparticle carriers. Whereas in vivo jetPEI displays poor penetration of tumor tissue, siRNA-$L_2$ distributes homogeneously throughout tumor tissue and achieves consistently high uptake in tumor cells. The capacity of siRNA-$L_2$ to offer superior tumor penetration is particularly significant given the highly inconsistent nature of clinical tumor vasculature and tissue morphology which limits consistent nanoparticle distribution. Here, we note that the PDX mouse model is less permissive to delivery than the orthotopic model. PDX models are considered more clinically relevant, as they preserve the native tissue architecture of the primary tumor through multiple in vivo passages and consistently recapitulate histopathologic and molecular characteristics, including drug responses and metastatic potential. The more challenging nature of the PDX model relative to the orthotopic model [which is considered more stringent than the flank model] aligns with recent discussion suggesting that the permeable nature of commonly used mouse tumor models has led to an overestimation of the EPR effect. Whereas nanocarriers like in vivo jetPEI may achieve efficacy in highly vascularized or nonsolid tumors, they lack the ability to diffuse throughout the bulk of tumor architecture. Faced with a more difficult delivery challenge in the PDX model, siRNA-$L_2$ maintains tumor accumulation better than does in vivo jetPEI. As the majority of human solid tumors contain regions of poor vascularization and display disparity in vessel permeability, the performance of siRNA-$L_2$ in the PDX model suggests applicability to a much broader range of cancers. A recognition of the limitations of the EPR effect and a developing understanding of tumor heterogeneity calls for innovative solutions for systemic RNAi cancer therapies. siRNA-$L_2$ deviates enormously from the standard nanoparticle format, and its notable advantages should inspire further research into similar conjugate-based strategies.

In situ targeting of albumin as an endogenous carrier is a powerful strategy to enhance the bioavailability of siRNA and avoid the issues associated with synthetic nanocarriers. siRNA-$L_2$ surpasses conventional delivery systems in circulation persistence, safety, biodistribution profile, and tumor penetration and cellular internalization. Ultimately, siRNA-$L_2$ achieves sustained gene silencing in tumors in vivo, providing strong proof-of-concept for therapeutic efficacy. This work highlights the immense value of the siRNA-$L_2$ conjugate as a translational and potentially transformative approach to improve i.v. RNAi cancer therapies.

Materials and Methods

Materials. Amine-modified single-stranded DNA (modification at 5' end) or RNA (modification at 3' end) and complementary single-stranded Cy5-, unmodified DNA, or unmodified RNA was obtained from Integrated DNA Technologies (for DNA) or GE Dharmacon. The pGreenFirel-CMV plasmid was obtained from System Biosciences, and packaging plasmids pMDLg/pRRE, pRSV-Rev, and pMD2.G were purchased from Addgene. In vivo jetPEI was purchased from VWR International. 1,2-distearoyl-sn-glycero-3-phosphoethanolamine-N-[azido(polyethylene glycol)-2000] (DSPE-PEG2000-azide) was purchased from Avanti Polar Lipids. NucBlue Fixed Cell ReadyProbes were purchased from Life Technologies. NAP-25 filtration columns were purchased from Fisher Scientific. RNeasy Mini Kit was purchased from Qiagen, iScript cDNA Synthesis Kit from BioRad Laboratories, and Caspase-Glo 3/7 Assay from Promega Corporation. All other reagents were purchased from Sigma-Aldrich.

Oligonucleotide-$L_2$ Synthesis. Single-stranded amine-modified oligo was reacted with 10-fold molar excess of dibenzocyclooctyne-PEG4-N-hydrox-ysuccinimidyl ester (DBCO-PEG4-NHS) predissolved at 25 mM in DMSO. The reaction was carried out for 18 h at room temperature at a 1 mM oligonucleotide concentration in 30% DMSO and 70% PBS with 8 mM TEA. The product was diluted threefold in water and filtered twice through NAP-25 columns, lyophilized, and then reacted with fivefold molar excess of DSPE-PEG2000-azide for 24 h at a 0.1 mM oligonucleotide concentration in 50% methanol, 50% water. The reaction was diluted and filtered one time through an NAP-25 column and then purified with reversed-phase HPLC using a Clarity Oligo-RP column (Phenomenex) under a linear gradient from 95% water (50 mM triethylammonium acetate), 5% methanol to 100% methanol. The conjugate molecular weight was confirmed using MALDI-TOF mass spectrometry (Voyager-DE STR Workstation) using 50 mg/mL 3-hydroxypicolinic acid in 50% water, 50% acetonitrile with 5 mg/mL ammonium citrate as a matrix. The yield of the oligo-$L_2$ was quantified based on absorbance at 260 nm. The purified oligo-$L_2$ was annealed to its complementary strand to generate Cy5-, unmodified DNA-$L_2$, or siRNA-$L_2$. Conjugation and annealing was also confirmed via agarose gel electrophoresis.

DNA was used as a cost-effective analog for siRNA in imaging studies, and is referred to as siRNA/siRNA-$L_2$ in the example for simplicity and cohesion (except where the figure is intended to show a direct comparison between DNA and siRNA). DNA/siRNA and DNA-$L_2$/siRNA-$L_2$ exhibited degradation on similar time scales (FIGS. 3E-F) and DNA-$L_2$ exhibits similar albumin binding (FIG. 2A), validating its use as a model for siRNA-$L_2$.

Oligonucleotide-$L_2$ characterization. Critical micelle concentration of oligo-$L_2$ was assessed fluorescently using Nile red, as described previously. Briefly, different dilutions were prepared from a 1 mg/mL stock solution to obtain micelle samples ranging in concentration from 0.0001 to 1 mg/mL Then, 10 µL of a 1 mg/mL Nile red stock solution in methanol was added to 1 mL of each sample and incubated overnight in the dark at room temperature. The next day, samples were filtered with a 0.45-µm syringe filter, and Nile red fluorescence was measured in 96-well plates using a microplate reader (Tecan Infinite 500, Tecan Group Ltd.) at an excitation wavelength of 535±20 nm and an emission wavelength of 612±25 nm. The CMC was Q:20 defined, as previously described, as the intersection point on the plot of the Nile red fluorescence versus the copolymer concentration.

Degradation of siRNA and siRNA-$L_2$ was assessed by incubation in 60% FBS for 4 h, 2 h, 1 h, 30 min, or 15 min and evaluation by agarose gel electrophoresis with comparison with a control sample in water.

Evaluation of albumin binding to oligo-$L_2$ in vitro. PAGE gel migration assay was used to assess binding of oligo-$L_2$ to BSA. 4-20% Mini-Protean TGX Precast Q:21 Gel were run in the Tetra Blotting Module (BioRad). siRNA, siRNA-$L_2$, DNA, and DNA-$L_2$ were incubated with varying amounts of BSA for 15 min. PAGE gels were stained using GelRed Nucleic Acid Stain (Biotium) according to manufacturer protocol and imaged under UV light for visualization of nucleic acid migration. Gels were subsequently stained with Coomassie blue to evaluate BSA migration.

PAGE gel migration assay was used to assess binding of oligo-$L_2$ to albumin in serum. siRNA or siRNA-$L_2$ was incubated with 9- or 13-fold molar excess BSA or 50% or 75% FBS (for approximate matching of mass of protein loaded per well). siRNA and siRNA-$L_2$ were imaged under UV light after poststaining with GelRed. Serum proteins were stained with Coomassie blue.

Isothermal calorimetry (ITC) experiments were performed using a TA Instruments Nano ITC. Oligo-$L_2$ was prepared at a concentration of 0.1 mM and BSA was dissolved at a concentration of 0.25 mM from lyophilized powder in PBS. Titration experiments were carried out at 37° C. with a 300-initial delay, 150-rpm stirring speed, and a sample cell volume (containing DNA-$L_2$) of 300 µL. Each injection was 2 µL, with an injection interval of 180 s. Data were analyzed using an independent binding site model with a blank constant correction incorporated to account for heat of dilution. All data analysis was performed in Nano ITC software.

Cell Culture. Human epithelial breast cancer cells (MDA-MB-231) were cultured in DMEM (Gibco Cell Culture) supplemented with 10% FBS (Gibco) and 0.1% gentamicin (Gibco). Luciferase-expressing MDA-MB-231s were generated as previously described.

In Vitro Gene Silencing. MDA-MB-231s were treated with siRNA or siRNA-$L_2$ complexed with in vivo jetPEI according to the manufacturer's protocol. The siRNA was either designed against the luciferase gene (luc siRNA) or was a scrambled sequence (scr siRNA). Cells were seeded at 2,000 cells/well in 96-well black-walled plates and allowed to adhere overnight. Cells were then treated in 10% serum for 24 h at a dose of 100 or 50 nM siRNA. After 24 h, media was replaced with luciferin-containing media (150 µg/mL) before imaging with an IVIS Lumina III imaging system at 24 and 48 h.

To evaluate silencing of a therapeutically relevant gene, siRNA targeting induced MCL-1 was used. MCF7 cells were treated with MCL-1-targeted or a scrambled control siRNA-$L_2$ at 200 nM in 10% serum-containing media for 24 h. At 48 h, RNA was harvested and MCL-1 mRNA levels were evaluated using quantitative real time PCR. In parallel, caspase activity was measured at 48 h using the Caspase Glo 3/7 Assay (Promega) according to the manufacturer's protocol.

Evaluation of albumin binding to oligo-$L_2$ in vivo. Fluorescent (Cy-5-labeled) DNA and DNA-$L_2$ was injected into the tail vein of CD-1 mice (4-6-wk-old, Charles Rivers Laboratories) at 1 mg/kg. Blood was collected at 20 min postinjection, and serum was isolated. Serum from mice injected with DNA, DNA-$L_2$, or saline was evaluated via PAGE gel migration assay was used to assess binding of oligo-$L_2$ to albumin in vivo.

In vitro evaluation using tumor spheroids. MCF7 cells (ATCC) were cultured in DMEM supplemented with 1% penicillin-streptomycin and 10% FBS. Three-dimensional MCF7 spheroid cultures were established as described previously. Briefly, cells were grown to 50% confluence in 2D culture. Cells were washed twice with trypsin (0.05%, Gibco), trypsin was aspirated, and cells were incubated at 37° C. for 10-15 min. Cells were resuspended in growth medium, pipetted to generate single-cell suspensions, and counted (Bio-Rad TC20 Automated Cell Counter). Single-cell suspensions (7,500 cells per 500 μL) were seeded in eight-well chamber slides (Nunc Lab-Tek II) precoated with 10 μL growth-factor-reduced Matrigel (BD Biosciences) in growth media containing 2% growth-factor-reduced Matrigel and cultured for 5 d. The 8-well chamber slides were used for evaluation by confocal microscopy; the setup was scaled up to 12-well plates for flow cytometry and gene silencing studies and down to 96-well plates for cytotoxicity studies.

To evaluate tumor spheroid penetration by confocal microscopy, on day 5, cultures were treated with 100 nM Cy5-labeled DNA, DNA-$L_2$, or DNA complexed with in vivo jetPEI for 4 h in fresh growth medium. Cultures were washed once with PBS and fixed for 2 min with BD Cyotfix/Cytoperm solution (BD Biosciences). After aspirating fixative and removing plastic chamber, cultures on slides were mounted with ProLong Gold Antifade with DAPI (Molecular Probes) and secured by coverslip. Slides were stored at 4° C. before confocal imaging. Confocal imaging was performed using the Nikon C1si+ system on a Nikon Eclipse Ti-0E inverted microscopy base. The PMT HV gain, laser power, and display settings were set for maximal SNR based on control biological samples such that negative control samples lacking label had no background fluorescence and treatment samples had no saturated pixels. Image acquisition and analysis were performed using Nikon NIS-Elements AR version 4.30.01.

To evaluate tumor spheroid penetration by flow cytometry, on day 5, cultures were treated as described above. Cultures were washed once with PBS and tumor cells were dissociated from Matrigel for evaluation of Cy5 fluorescence.

Blood Plasma Pharmacokinetics. Fluorescent (Cy-5-labeled) DNA and DNA-$L_2$ were injected into the tail vein of CD-1 mice (4-6-wk-old, Charles Rivers Laboratories) at 1 mg/kg. Before injection, the mouse ear was placed on a coverslip on the Nikon C1si+ confocal microscope system. An artery within the ear was set in focus, and after injection, images of the artery were automatically collected every 2 s for 30 min. After 30 min, animals were killed. Maximum initial fluorescence of the artery was set to a time of 0 s. Artery fluorescence was evaluated by quantifying a circular ROI entirely within the vessel. Data were fit to a one-phase exponential decay model (equation below) and half-life and area under the curve were determined from these fits.

$$\text{Fluorescence}_{blood} = \text{Fluor}_0 * e^{-kt}.$$

Biodistribution in Tumor-Bearing Mice. For the orthotopic mouse tumor model, athymic nude female mice (4-6-wk-old, Jackson Laboratory) were injected in each mammary fat pad with $1 \times 10^6$ MDA-MB-231 cells in DMEM: Matrigel (50:50). After 21 d, tumor-bearing mice were injected via the tail vein with 1 mg/kg (nucleic acid dose) of fluorescent DNA, DNA-$L_2$, or DNA loaded in in vivo jetPEI. After 30 min, 24 h, and 48 h, animals were killed and the organs of interest (heart, lungs, liver, spleen, kidneys, and tumors) were excised. The fluorescence intensity in the organs was quantified on an IVIS Lumina III imaging system at excitation wavelength of 620±5 nm and emission wavelength of 670±5 nm (n=3 animals, n=6 tumors). Tumor radiance data were fit to a one-phase exponential decay model (equation below), and area under the curve was determined from these fits.

$$\text{Radiance}_{tumor} = \text{Radiance}_0 * e^{-kt}.$$

For the PDX mouse tumor model, the triple-negative line HCI-010 was transplanted into one inguinal mammary fat pad (surgically cleared of endogenous epithelium) of NOD-SCID (Jackson Laboratory) female mice of Q:26 3-4 wk of age (64). After ~8 wk, PDX tumors were harvested, cut into 4 mm×2-mm pieces, serially transplanted into the cleared inguinal mammary fat pads of a new cohort of NOD-SCID female mice, and grown to a volume of 300-500 $mm^3$. Tumor-bearing mice were injected via the tail vein with 1 mg/kg (nucleic acid dose) of fluorescent DNA-$L_2$ or DNA loaded in in vivo jetPEI. After 24 h, animals were killed, and the organs of interest (heart, lungs, liver, spleen, kidneys, and tumors) were excised. The fluorescence intensity in the organs was quantified on an IVIS Lumina III imaging system at excitation wavelength of 620±5 nm and emission wavelength of 670±5 nm (n=2 animals, n=2 tumors).

Acute Toxicity in Liver and Kidney. CD31 mice were injected with siRNA-$L_2$ (10 mg/kg) or in vivo jetPEI-loaded siRNA (1, 2 mg/kg). After 24 h, blood was collected by cardiac puncture and then centrifuged at 2,000×g for 5 min. Then, Q:27 plasma was harvested and tested by the Vanderbilt Translational Pathology Shared Resource for systemic levels of ALT, AST, BUN, and creatinine.

Tumor Distribution in Vivo After i.v. Injection. For the orthotopic tumor model, athymic nude female mice (4-6-wk-old, Jackson Laboratory) were injected in each mammary fat pad with $1 \times 10^6$ MDA-MB-231 cells in DMEM: Matrigel (50:50). After 21 d, tumor-bearing mice were injected via the tail vein with saline, 1 or 10 mg/kg fluorescent DNA-$L_2$, or 1 mg/kg DNA loaded in in vivo jetPEI. Tumors were excised, and cells were isolated from each tumor. A mixture of collagenase and DNase was used to dissociate cells, and ammonium-chloride-potassium lysing buffer was used to lyse red blood cells. Uptake of fluorescent DNA or DNA-$L_2$ was evaluated by flow cytometry (n=4 animals, n=8 tumors). Tumor cells were identified as the cell population expressing GFP, whereas the GFP-negative cell population corresponded to native mouse cells.

Target Gene Silencing After i.v. Injection. Athymic nude female mice (4-6-wk-old, Jackson Laboratory) were injected in each mammary fat pad with $1 \times 10^6$ MDA-MB-231 cells in DMEM:Matrigel (50:50). After tumors reached a size of 50 $mm^2$, tumor-bearing mice were injected i.p. with luciferin substrate (150 mg/kg) and imaged for bioluminescence on an IVIS Lumina III imaging system 30 min postinjection.

Next, the mice were injected via the tail vein with 10 mg/kg (based on siRNA dose) luc siRNA or siRNA-$L_2$ or an scr siRNA-$L_2$. Alternatively, mice were injected with 1 mg/kg in vivo jetPEI complexed with luc or scr siRNA. Mice were imaged and treated at days 0 and 1 following treatment injection and imaged for bioluminescence over time. Relative luminescence was determined by measuring the raw luminescent intensity of each tumor on each day and comparing to the initial signal at day 0 (n=10 tumors per group). Mouse body weight was evaluated at each of these time points to investigate treatment toxicity.

Statistical Methods. The treatment groups were statistically compared using a one-way ANOVA test (for nonrepeated measures of more than two groups) or a two-way ANOVA (for measures repeated at multiple time points) coupled with a Tukey means comparison test. For comparison between two groups, an independent two-tailed t test was used. A P value <0.05 was deemed representative of a significant difference between groups. For all data shown, the arithmetic mean and SE are reported, and the sample size (n) is indicated.

REFERENCES

1. Soutschek J, et al. (2004) Therapeutic silencing of an endogenous gene by systemic administration of modified siRNAs. *Nature* 432:173-178.
2. Davis M E, et al. (2010) Evidence of RNAi in humans from systemically administered siRNA via targeted nanoparticles. *Nature* 464:1067-1070.
3. Oe Y, et al. (2014) Actively-targeted polyion complex micelles stabilized by cholesterol and disulfide cross-linking for systemic delivery of siRNA to solid tumors. *Biomaterials* 35:7887-7895.
4. Miteva M, et al. (2015) Tuning PEGylation of mixed micelles to overcome intracellular and systemic siRNA delivery barriers. *Biomaterials* 38:97-107.
5. Sarett S (2016) Hydrophobic interactions between polymeric carrier and palmitic acid-conjugated siRNA improve pegylated polyplex stability and enhance in vivo pharmacokinetics and tumor gene silencing. *Biomaterials* 97:122-32.
6. Lv H, Zhang S, Wang B, Cui S, Yan J (2006) Toxicity of cationic lipids and cationic polymers in gene delivery. *J Controlled Release* 114:100-109.
7. Akhtar S, Benter I (2007) Toxicogenomics of non-viral drug delivery systems for RNAi: Potential impact on siRNA-mediated gene silencing activity and specificity. *Adv Drug Deliv Rev* 59:164-182.
8. Owens D E, 3rd, Peppas N A (2006) Opsonization, biodistribution, and pharmacokinetics of polymeric nanoparticles. *Int J Pharm* 307:93-102.
9. Østergaard M E, et al. (2015) Efficient synthesis and biological evaluation of 5'-galnac conjugated antisense oligonucleotides. *Bioconjug Chem* 26:1451-1455.
10. Kubo T, Takei Y, Mihara K, Yanagihara K, Seyama T (2012) Amino-modified and lipid-conjugated dicer-substrate siRNA enhances RNAi efficacy. *Bioconjug Chem* 23: 164-173.
11. Lorenz C, Hadwiger P, John M, Vornlocher H P, Unverzagt C (2004) Steroid and lipid conjugates of siRNAs to enhance cellular uptake and gene silencing in liver cells. *Bioorg Med Chem Lett* 14:4975-4977.
12. Dobrovolskaia M A A P, Aggarwal P, Hall J B, McNeil S E (2008) Preclinical studies to understand nanoparticle interaction with the immune system and its potential effects on nanoparticle biodistribution. *Mol Pharm* 5:487-495.
13. Shi J X Z, Kamaly N, Farokhzad O C (2011) Self-assembled targeted nanoparticles: Evolution of technologies and bench to bedside transition. *Acc Chem Res* 44:1123-1134.
14. Wolfrum C, et al. (2007) Mechanisms and optimization of in vivo delivery of lipophilic siRNAs. *Nat Biotechnol* 25:1149-1157.
15. Matsuda S, et al. (2015) siRNA conjugates carrying sequentially assembled trivalent N-acetylgalactosamine linked through nucleosides elicit robust gene silencing in vivo in hepatocytes. *ACS Chem Biol* 10:1181-1187.
16. Rajeev K G, et al. (2015) Hepatocyte-specific delivery of siRNAs conjugated to novel non-nucleosidic trivalent N-acetylgalactosamine elicits robust gene silencing in vivo. *ChemBioChem* 16:903-908.
17. Commisso C, et al. (2013) Macropinocytosis of protein is an amino acid supply route in Ras-transformed cells. *Nature* 497:633-637.
18. Kamphorst J J, et al. (2015) Human pancreatic cancer tumors are nutrient poor and tumor cells actively scavenge extracellular protein. *Cancer Res* 75:544-553.
19. Danhier F (2016) To exploit the tumor microenvironment: Since the EPR effect fails in the clinic, what is the future of nanomedicine? *J Control Release* 244:108-121.
20. Nichols J W, Bae Y H (2014) EPR: Evidence and fallacy. *J Control Release* 190:451-464.
21. Prabhakar U, et al. (2013) Challenges and key considerations of the enhanced permeability and retention effect for nanomedicine drug delivery in oncology. *Cancer Res* 73:2412-2417.
22. Jain R K, Stylianopoulos T (2010) Delivering nanomedicine to solid tumors. *Nat Rev Clin Oncol* 7:653-664.
23. Bae Y H, Park K (2011) Targeted drug delivery to tumors: Myths, reality and possibility. *J Control Release* 153:198-205.
24. Eliasof S, et al. (2013) Correlating preclinical animal studies and human clinical trials of a multifunctional, polymeric nanoparticle. *Proc Natl Acad Sci USA* 110: 15127-15132.
25. Zuckerman J E, et al. (2014) Correlating animal and human phase 1a/1b clinical data with CALAA-01, a targeted, polymer-based nanoparticle containing siRNA. *Proc Natl Acad Sci USA* 111:11449-11454.
26. Kai M P, et al. (2016) Tumor presence induces global immune changes and enhances nanoparticle clearance. *ACS Nano* 10:861-870.
27. Dong Y, et al. (2014) Lipopeptide nanoparticles for potent and selective siRNA delivery in rodents and non-human primates. *Proc Natl Acad Sci USA* 111:3955-3960.
28. Martin J D, Fukumura D, Duda D G, Boucher Y, Jain R K (2016) Reengineering the tumor microenvironment to alleviate hypoxia and overcome cancer heterogeneity. *Cold Spring Harb Perspect Med* 6:a027094.
29. Reuter K G, et al. (2015) Targeted print hydrogels: The role of nanoparticle size and ligand density on cell association, biodistribution, and tumor accumulation. *Nano Lett* 15:6371-6378.
30. Tong R, Langer R (2015) Nanomedicines targeting the tumor microenvironment. *Cancer J* 21:314-321.
31. Clark A J W D, et al. (2016) CRLX101 nanoparticles localize in human tumors and not in adjacent, nonneoplastic tissue after intravenous dosing. *Proc Natl Acad Sci USA* 113: 3850-3854.

32. Hammond P T (2016) Shooting for the moon: Nanoscale approaches to cancer. *ACS Nano* 10:1711-1713.
33. Wong C, et al. (2011) Multistage nanoparticle delivery system for deep penetration into tumor tissue. *Proc Natl Acad Sci USA* 108:2426-2431.
34. Ernsting M J, Murakami M, Roy A, Li S D (2013) Factors controlling the pharmacokinetics, biodistribution and intratumoral penetration of nanoparticles. *J Control Release* 172:782-794.
35. Kratz F (2008) Albumin as a drug carrier: Design of prodrugs, drug conjugates and nanoparticles. *J Control Release* 132:171-183.
36. Qin S, et al. (2014) A physiological perspective on the use of imaging to assess the in vivo delivery of therapeutics. *Ann Biomed Eng* 42:280-298.
37. Neumann E, et al. (2010) Native albumin for targeted drug delivery. Expert Opin Drug Deliv 7:915-925.
38. Cohen J L C J, et al. (1998) Improved left ventricular endocardial border delineation and opacification with OPTISON (FS069), a new echocardiographic contrast agent. Results of a phase III Multicenter Trial. *J Am Coll Cardiol* 32:746-752.
39. Kuwahara H, et al. (2011) Efficient in vivo delivery of siRNA into brain capillary endothelial cells along with endogenous lipoprotein. *Mol Ther* 19:2213-2221.
40. Nakayama T, et al. (2012) Harnessing a physiologic mechanism for siRNA delivery with mimetic lipoprotein particles. *Mol Ther* 20:1582-1589.
41. Uno Y, et al. (2011) High-density lipoprotein facilitates in vivo delivery of α-tocopherol-conjugated short-interfering RNA to the brain. *Hum Gene Ther* 22:711-719.
42. Bienk K, et al. (2016) An albumin-mediated cholesterol design-based strategy for tuning sirna pharmacokinetics and gene silencing. *J Control Release* 232:143-151.
43. Lau S, et al. (2012) Enhanced extravasation, stability and in vivo cardiac gene silencing via in situ siRNA-albumin conjugation. *Mol Pharm* 9:71-80.
44. Liu H, et al. (2014) Structure-based programming of lymph-node targeting in molecular vaccines. *Nature* 507: 519-522.
45. Levy O E, et al. (2014) Novel exenatide analogs with peptidic albumin binding domains: Potent anti-diabetic agents with extended duration of action. *PLoS One* 9: e87704.
46. Chen H, et al. (2016) Chemical conjugation of evans blue derivative: A strategy to develop long-acting therapeutics through albumin binding. *Theranostics* 6:243-253.
47. Wilhelm S, et al. (2016) Analysis of nanoparticle delivery to tumours. *Nat Rev Mater* 1: 16014.
48. Sidi A A, et al. (2008) Phase VII marker lesion study of intravesical BC-819 DNA plasmid in H19 over expressing superficial bladder cancer refractory to bacillus Calmette-Guerin. *J Urol* 180:2379-2383.
49. Sarett S M, Kilchrist K V, Miteva M, Duvall C L (2015) Conjugation of palmitic acid improves potency and longevity of siRNA delivered via endosomolytic polymer nano-particles. *J Biomed Mat Res A* 103:3107-3116.
50. Ambardekar V V, et al. (2011) The modification of siRNA with 3' cholesterol to increase nuclease protection and suppression of native mRNA by select siRNA polyplexes. *Biomaterials* 32:1404-1411.
51. McArthur M J A B, et al. (1999) Cellular uptake and intracellular trafficking of long chain fatty acids. *J Lipid Res* 40:1371-1383.
52. Trigatti B L G G, Gerber G E (1995) A direct role for serum albumin in the cellular uptake of long-chain fatty acids. *Biochem J* 308:155-159.
53. Zuckerman J E, Choi C H, Han H, Davis M E (2012) Polycation-siRNA nanoparticles can disassemble at the kidney glomerular basement membrane. *Proc Natl Acad Sci USA* 109:3137-3142.
54. Ozpolat B, Sood A K, Lopez-Berestein G (2014) Liposomal siRNA nanocarriers for cancer therapy. *Adv Drug Deliv Rev* 66:110-116.
55. Behlke M A (2008) Chemical modification of siRNAs for in vivo use. *Oligonucleotides* 18:305-319.
56. Rettig G R, Behlke M A (2012) Progress toward in vivo use of siRNAs-II. *Mol Ther* 20: 483-512.
57. Park J, Park J, Pei Y, Xu J, Yeo Y (2016) Pharmacokinetics and biodistribution of recently-developed siRNA nanomedicines. *Adv Drug Deliv Rev* 104:93-109.
58. Chen Y, et al. (2014) Highly effective inhibition of lung cancer growth and metastasis by systemic delivery of siRNA via multimodal mesoporous silica-based nanocarrier. *Biomaterials* 35:10058-10069.
59. Lee M S, et al. (2014) Target-specific delivery of sirna by stabilized calcium phosphate nanoparticles using dopa-hyaluronic acid conjugate. *J Control Release* 192: 122-130.
60. Choi KYSO, et al. (2014) Versatile RNA interference nanoplatform for systemic delivery of RNAs. *ACS Nano* 8:4559-4570.
61. Zhu X, et al. (2015) Long-circulating siRNA nanoparticles for validating Prohibitin1-targeted non-small cell lung cancer treatment. *Proc Natl Acad Sci USA* 112:7779-7784.
62. Bartlett D W, Su H, Hildebrandt U, Weber W A, Davis M E (2007) Impact of tumor-specific targeting on the biodistribution and efficacy of siRNA nanoparticles measured by multimodality in vivo imaging. *Proc Natl Acad Sci USA* 104:15549-15554.
63. Nagy J A, et al. (2006) Permeability properties of tumor surrogate blood vessels induced by VEGF-A. *Lab Invest* 86:767-780.
64. DeRose Y S, et al. (2013) Patient-derived models of human breast cancer: Protocols for in vitro and in vivo applications in tumor biology and translational medicine. *Curr Protoc Pharmacol Chapter* 14:Unit 14.23.
65. Gupta M K, Meyer T A, Nelson C E, Duvall C L (2012) Poly(P S-b-DMA) micelles for reactive oxygen species triggered drug release. *J Control Release* 162:591-598.
66. Fowler S D G P (1985) Application of nile red, a fluorescent hydrophobic probe, for the detection of neutral lipid deposits in tissue sections. *J Histochem Cytochem* 33:833-836.
67. Coutinho, Paulo J G; Castanheira, Elisabete M S; Ceu Rei, M; Real Oliveira, M Elisabete C D (2002) Nile red and DCM fluorescence anisotropy studies in $C_{12}E_7$/DPPC mixed systems. *J Phys Chem B,* 106:12841-12846.
68. Debnath J, Muthuswamy S K, Brugge J S (2003) Morphogenesis and oncogenesis of MCF-10A mammary epithelial acini grown in three-dimensional basement membrane cultures. *Methods* 30:256-268.
69. Brantley-Sieders D M, et al. (2011) Angiocrine factors modulate tumor proliferation and motility through EphA2 repression of Slit2 tumor suppressor function in endothelium. *Cancer Res* 71:976-987.
70. National Research Council (2011) *Guide for the Care and Use of Laboratory Animals* (National Academies Press, Washington, DC), 8th Ed.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A compound comprising siRNA functionalized with a dibenzocyclooctyne moiety and directly conjugated to 1,2-distearoyl-sn-glycero-3-phosphoethanolamine-N-[azido(polyethylene glycol)-2000].

2. The compound of claim 1, wherein the compound is complexed with albumin.

3. The compound of claim 1, wherein the siRNA comprises a guide sequence that is complementary to an antisense sequence.

* * * * *